(12) United States Patent
Dyballa et al.

(10) Patent No.: US 9,643,987 B2
(45) Date of Patent: *May 9, 2017

(54) MONOPHOSPHITES HAVING AN UNSYMMETRIC BIARYL UNIT

(71) Applicant: Evonik Degussa GmbH, Essen (DE)

(72) Inventors: Katrin Marie Dyballa, Recklinghausen (DE); Robert Franke, Marl (DE); Detlef Selent, Rostock (DE); Armin Börner, Rostock (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/957,074

(22) Filed: Dec. 2, 2015

(65) Prior Publication Data

US 2016/0159838 A1   Jun. 9, 2016

(30) Foreign Application Priority Data

Dec. 4, 2014  (EP) .................................... 14196197

(51) Int. Cl.
| | | |
|---|---|---|
| C07F 15/00 | (2006.01) | |
| C07F 15/06 | (2006.01) | |
| C07F 9/6574 | (2006.01) | |
| C07C 45/50 | (2006.01) | |

(52) U.S. Cl.
CPC .......... *C07F 9/65744* (2013.01); *C07C 45/50* (2013.01); *C07F 15/008* (2013.01); *C07F 15/0033* (2013.01); *C07F 15/0046* (2013.01); *C07F 15/0073* (2013.01); *C07F 15/06* (2013.01)

(58) Field of Classification Search
CPC .............. C07F 9/65744; C07F 15/0073; C07F 15/0046; C07F 15/0033; C07F 15/008; C07F 15/06; C07C 45/50
USPC ........................... 556/13, 12; 568/12; 268/13
See application file for complete search history.

(56) References Cited

U.S. PATENT DOCUMENTS

| | | |
|---|---|---|
| 4,599,206 A | 7/1986 | Billig et al. |
| 2015/0290633 A1 | 10/2015 | Christiansen et al. |
| 2016/0159718 A1* | 6/2016 | Dyballa ................ B01J 31/185 556/13 |

FOREIGN PATENT DOCUMENTS

| | | |
|---|---|---|
| WO | WO 85/03702 A1 | 8/1985 |
| WO | WO 2004/076464 A2 | 9/2004 |
| WO | WO 2014/056733 A1 | 4/2014 |

OTHER PUBLICATIONS

Extended European Search Report issued Jun. 8, 2015 in Patent Application No. 14196197.9 (with English translation of categories of cited documents).

Peter Hannen, et al., "New monodentate chiral phosphite ligands for asymmetric hydrogenation," Chemical Communications, XP055191367, Jul. 22, 2003, pp. 2210-2211.

* cited by examiner

*Primary Examiner* — Porfirio Nazario Gonzalez
(74) *Attorney, Agent, or Firm* — Oblon, McClelland, Maier & Neustadt, L.L.P.

(57) ABSTRACT

Monophosphites having an unsymmetric biaryl structure and metal complexes thereof are provided. The metal complex compositions are useful as hydroformylation catalysts. The metals of the complex include Rh, Ru, Co and Ir. A method of hydroformylation using the metal complex or the metal complex components is also provided.

19 Claims, 1 Drawing Sheet

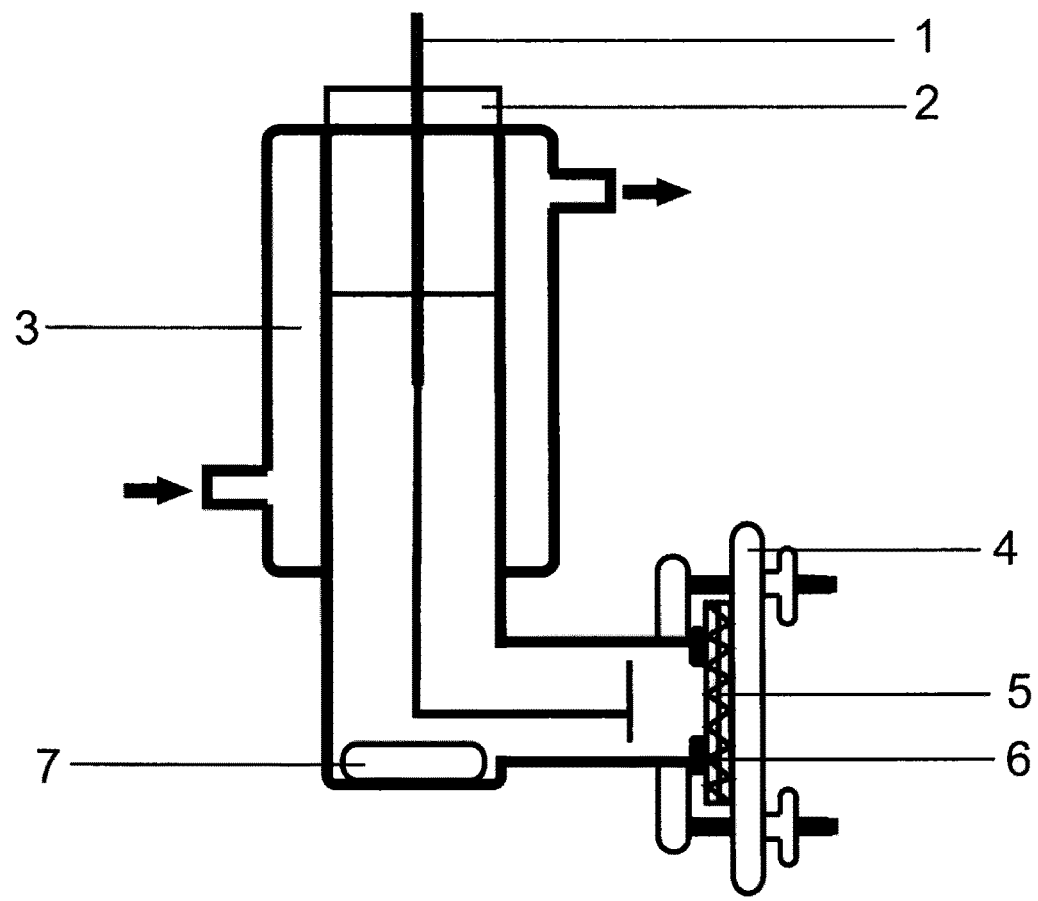

MONOPHOSPHITES HAVING AN UNSYMMETRIC BIARYL UNIT

CROSS REFERENCE TO RELATED APPLICATIONS

This application claims priority to European Application No. 14196197.9, filed Dec. 4, 2014, the disclosure of which is incorporated herein by reference in its entirety.

BACKGROUND OF THE INVENTION

Field of the Invention

The invention relates to monophosphites having an unsymmetric biaryl unit and their utility as ligands in hydroformylation.

The biaryl units of the invention have, for example, a phenyl-phenyl unit or a naphthyl-phenyl unit.

Discussion of the Background

The reactions between an olefin compound, carbon monoxide and hydrogen in the presence of a catalyst to give an aldehyde comprising one additional carbon atom are known as hydroformylation or oxo synthesis. In these reactions, compounds of the transition metals of group VIII of the periodic table of the elements are frequently employed as catalysts.

Known ligands include, compounds of the phosphine, phosphite and phosphonite classes each comprising trivalent phosphorus $P^{III}$. A good overview of the state of the hydroformylation of olefins can be found in B. CORNILS, W. A. HERRMANN, "Applied Homogeneous Catalysis with Organometallic Compounds", vol. 1 & 2, VCH, Weinheim, New York, 1996 or R. Franke, D. Selent, A. Börner, "Applied Hydroformylation", Chem. Rev., 2012, DOI: 10.1021/cr3001803.

The disadvantage of bi- and polydentate phosphine ligands is a relatively high level of complexity necessary for preparation thereof. It is therefore often unviable to use such systems in industrial processes. An additional factor is comparatively low activity, which has to be compensated for by chemical engineering, through high residence times. This in turn leads to unwanted side reactions of the products.

In Angew. Chem. Int. Ed. 2000, 39, No. 9, p. 1639-1641, Börner et al. describe ligands having one P—C bond and two P—O bonds; these are thus phosphonites. The phosphonites described therein, when used in hydroformylation, have n/iso selectivities (n/iso=the ratio of linear aldehyde (=n) to branched (=iso) aldehyde)) of 0.61 to 1.57.

The phosphonite ligands described in DE 199 54 721 have a good n/iso selectivity. However, in-house studies have shown that the compound II-c (in DE 199 54 721; page 6) has a tendency to photochemically induced breakdown, and should therefore not be used on the industrial scale.

One disadvantage of the ligands having a phosphonite structure is that their preparation is very complex. The possibility of a favourable and simple synthesis is crucial for the use of ligands in an industrial scale process.

The ease of availability and the associated likelihood of industrial scale use is an important criterion, since the preparation complexity and the associated costs that arise may only be so high if the viability of the overall process is to be obtained.

Rhodium-monophosphite complexes in catalytically active compositions are suitable for the hydroformylation of branched olefins having internal double bonds.

Since the 1970s, there have been descriptions of the use of "bulky phosphites" in hydroformylation (see, inter alia, van Leeuwen et al., Journal of Catalysis, 2013, 298, 198-205). These feature good activity, but the n/iso selectivity for terminally hydroformylated compounds is low and in need of improvement.

EP 0 155 508 discloses the use of bisarylene-substituted monophosphites in the rhodium-catalysed hydroformylation of sterically hindered olefins, e.g. isobutene. Rhodium concentrations used here are sometimes very high (one being 250 ppm), which is unacceptable for an industrial scale process in view of the current cost of rhodium and has to be improved.

Even though a multitude of ligands and the use thereof in rhodium-catalysed hydroformylation are known, it is desirable to develop new ligands having improved properties.

SUMMARY OF THE INVENTION

It was an object of the invention to provide monophosphites having advantageous properties compared to the known monophosphites in the hydroformylation reaction. One example of such a property may be an enhanced yield.

In particular, one object consists in providing novel ligands which, on use, lead to an improved yield compared to structurally related monophosphites likewise having a biaryl unit. The improved yield should be achieved for at least one olefin.

These and other objects are achieved by the present invention the first embodiment of which includes a monophosphite compound of structure (I) or (II):

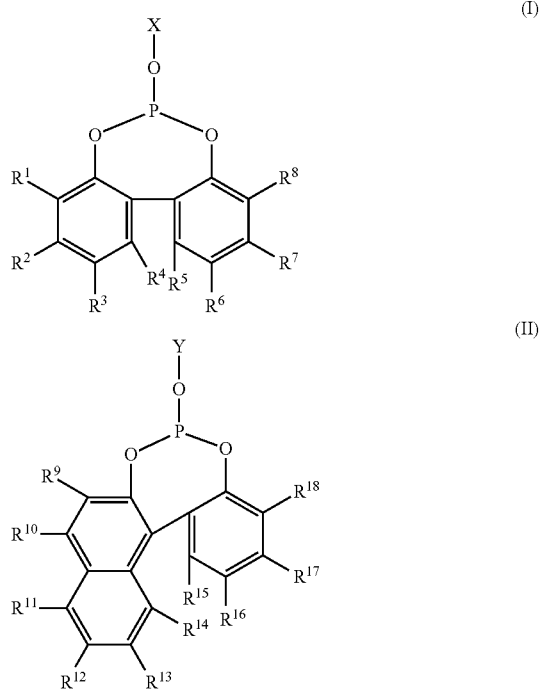

wherein
$R^1$, $R^2$, $R^3$, $R^4$, $R^5$, $R^6$, $R^7$, $R^8$ are each independently —H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —$SO_3H$, —CN, —$NH_2$, or —N[(C1-$C_{12}$)-alkyl]$_2$;

$R^9$, $R^{10}$, $R^{11}$, $R^{12}$, $R^{13}$, $R^{14}$, $R^{15}$, $R^{16}$, $R^{17}$, $R^{18}$ are each independently —H, —$(C_1-C_{12})$-alkyl, —O—$(C_1-C_{12})$-alkyl, —O—$(C_6-C_{20})$-aryl, —$(C_6-C_{20})$-aryl, —S-alkyl, —S-aryl, halogen, COO—$(C_1-C_{12})$-alkyl, CONH—$(C_1-C_{12})$-alkyl, —CO—$(C_1-C_{12})$-alkyl, —CO—$(C_6-C_{20})$-aryl, —COOH, —OH, —SO$_3$H, —NH$_2$, or —N[(C1-C$_{12}$)-alkyl]$_2$;

X and Y are each independently —$(C_1-C_{12})$-alkyl, —$(C_6-C_{20})$-aryl, —$(C_3-C_{12})$-cycloalkyl, or —$(C_3-C_{12})$-heterocycloalkyl, the two radicals in at least one of the four following radical pairs are not the same radical: $R^1$ and $R^8$, $R^2$ and $R^7$, $R^3$ and $R^6$, $R^4$ and $R^5$; and the $R^3$ and $R^4$ radicals are not joined to one another via a carbon chain;

wherein alkyl and aryl groups may optionally be substituted.

The feature "and the two radicals in at least one of the four following radical pairs are not the same radical: $R^1$ and $R^8$, $R^2$ and $R^7$, $R^3$ and $R^6$, $R^4$ and $R^5$" expresses the fact that this is an unsymmetric biaryl. The two aromatic systems may not be reflected onto one another by a mirror plane lying between them.

The following radical pairs are permitted, for example:
$R^1 \neq R^8$, $R^2 = R^7$, $R^3 = R^6$, $R^4 = R^5$;
$R^1 = R^8$, $R^2 = R^7$, $R^3 \neq R^6$, $R^4 = R^5$.

But also radical pairs in which more than just one pair is not the same, for example:
$R^1 \neq R^8$, $R^2 = R^7$, $R^3 \neq R^6$, $R^4 = R^5$;
$R^1 \neq R^8$, $R^2 \neq R^7$, $R^3 \neq R^6$, $R^4 = R^5$.

According to the present invention all four radical pairs cannot each be the same:
$R^1 = R^8$, $R^2 = R^7$, $R^3 = R^6$, $R^4 = R^5$.

This would be a symmetric biaryl.

$(C_1-C_{12})$-Alkyl and O—$(C_1-C_{12})$-alkyl may each be unsubstituted or substituted by one or more identical or different radicals selected from $(C_3-C_{12})$-cycloalkyl, $(C_3-C_{12})$-heterocycloalkyl, $(C_6-C_{20})$-aryl, fluorine, chlorine, cyano, formyl, acyl and alkoxycarbonyl.

$(C_6-C_{20})$-Aryl and —$(C_6-C_{20})$-aryl-$(C_6-C_{20})$-aryl- may each optionally be unsubstituted or substituted by one or more identical or different radicals selected from:

—H, —$(C_1-C_{12})$-alkyl, —O—$(C_1-C_{12})$-alkyl, —O—$(C_6-C_{20})$-aryl, —$(C_6-C_{20})$-aryl, -halogen (such as Cl, F, Br, I), —COO—$(C_1-C_{12})$-alkyl, —CONH—$(C_1-C_{12})$-alkyl, —$(C_6-C_{20})$-aryl-CON[$(C_1-C_{12})$-alkyl]$_2$, —CO—$(C_1-C_{12})$-alkyl, —CO—$(C_6-C_{20})$-aryl, —COOH, —OH, —SO$_3$H, —SO$_3$Na, —NO$_2$, —CN, —NH$_2$, —N[$(C_1-C_{12})$-alkyl]$_2$.

In another embodiment, the invention includes a metal complex, comprising the monophosphite compound of formula (I) or (II) and a metal selected from the group consisting of Rh, Ru, Co and Ir.

In a further embodiment the present invention includes a method for hydroformylation comprising conducting the hydroformylation reaction in the presence of the metal complex of the monophosphite compound of formula (I) or (II).

In addition, the hydroformylation further comprises: a) charging an olefin to a reaction device; b) adding a catalyst comprising the complex of claim 13 to the reaction device; or adding a catalyst comprising the monophosphite compound of claim 1 and a substance having a metal atom selected from the group consisting of Rh, Ru, Co and Ir; c) feeding H$_2$ and CO into the reaction device to the olefin and catalyst to obtain a reaction mixture; and d) heating the reaction mixture to effect conversion of the olefin to an aldehyde.

BRIEF DESCRIPTION OF DRAWINGS

The FIGURE shows a reaction apparatus in which the coupling reaction to give the corresponding unsymmetric biaryls can be conducted. The apparatus comprises a nickel cathode (1) and an anode composed of boron-doped diamond (BDD) on silicon (5). The apparatus can be cooled with the aid of a cooling jacket (3). The arrows indicate the flow direction of the cooling water. The reaction space is sealed by a Teflon stopper (2). The reaction mixture is mixed by a magnetic stirrer bar (7). On the anodic side, the apparatus is sealed by screw clamps (4) and seals (6).

DETAILED DESCRIPTION OF THE INVENTION

Any ranges mentioned herein below include all values and subvalues between the lowest and highest limit of the range.

In the context of the invention, the expression "—$(C_1-C_{12})$-alkyl" may encompass straight-chain and branched alkyl groups. Preferably, these groups are unsubstituted straight-chain or branched —$(C_1-C_8)$-alkyl groups and most preferably —$(C_1-C_6)$-alkyl groups. Examples of —$(C_1-C_{12})$-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The description relating to the expression "—$(C_1-C_{12})$-alkyl" also applies to the alkyl groups in —O—$(C_1-C_{12})$-alkyl, i.e. in —$(C_1-C_{12})$-alkoxy. Preferably, these groups are unsubstituted straight-chain or branched —$(C_1-C_6)$-alkoxy groups.

Substituted —$(C_1-C_{12})$-alkyl groups and substituted —$(C_1-C_{12})$-alkoxy groups may have one or more substituents, depending on their chain length. The substituents are preferably each independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl and alkoxycarbonyl.

The expression "—$(C_3-C_{12})$-cycloalkyl", in the context of the present invention, may include mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbornyl and adamantyl.

One example of a substituted cycloalkyl may be menthyl.

The expression "—$(C_3-C_{12})$-heterocycloalkyl groups", in the context of the present invention, may include nonaromatic saturated or partly unsaturated cycloaliphatic groups having 3 to 12, especially 5 to 12, carbon atoms. The —$(C_3-C_{12})$-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms may be replaced by heteroatoms or heteroatom-containing groups. The heteroatoms or the heteroatom-containing groups may preferably be selected from —O—, —S—, —N—, —N(=O)—, —C(=O)— and —S(=O)—. Examples of —$(C_3-C_{12})$-heterocycloalkyl groups include tetrahydrothiophenyl, tetrahydrofuryl, tetrahydropyranyl, menthyl and dioxanyl.

In the context of the present invention, the expression "—(C$_6$-C$_{20}$)-aryl and —(C$_6$-C$_{20}$)-aryl-(C$_6$-C$_{20}$)-aryl-" encompasses mono- or polycyclic aromatic hydrocarbyl radicals. These have 6 to 20 ring atoms, more preferably 6 to 14 ring atoms, especially 6 to 10 ring atoms. Aryl is preferably —(C$_6$-C$_{10}$)-aryl and —(C$_6$-C$_{10}$)-aryl-(C$_6$-C$_{10}$)-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —(C$_6$-C$_{20}$)-aryl groups and —(C$_6$-C$_{20}$)-aryl-(C$_6$-C$_{20}$)-aryl groups may have one or more (e.g. 1, 2, 3, 4 or 5) substituents, depending on the ring size. These substituents may preferably each independently be selected from —H, —(C$_1$-C$_{12}$)-alkyl, —O—(C$_1$-C$_{12}$)-alkyl, —O—(C$_6$-C$_{20}$)-aryl, —(C$_6$-C$_{20}$)-aryl, -halogen (such as Cl, F, Br, I), —COO—(C$_1$-C$_{12}$)-alkyl, —CONH—(C$_1$-C$_{12}$)-alkyl, —(C$_6$-C$_{20}$)-aryl-CON[(C$_1$-C$_{12}$)-alkyl]$_2$, —CO—(C$_1$-C$_{12}$)-alkyl, —CO—(C$_6$-C$_{20}$)-aryl, —COOH, —OH, —SO$_3$H, —SO$_3$Na, —NO$_2$, —CN, —NH$_2$, and —N[(C$_1$-C$_{12}$)-alkyl]$_2$.

Substituted —(C$_6$-C$_{20}$)-aryl groups and —(C$_6$-C$_{20}$)-aryl-(C$_6$-C$_{20}$)-aryl groups are preferably substituted —(C$_6$-C$_{10}$)-aryl groups and —(C$_6$-C$_{10}$)-aryl-(C$_6$-C$_{10}$)-aryl groups, especially substituted phenyl or substituted naphthyl or substituted anthracenyl. Substituted —(C$_6$-C$_{20}$)-aryl groups preferably bear one or more, for example 1, 2, 3, 4 or 5, substituents selected from —(C$_1$-C$_{12}$)-alkyl groups, —(C$_1$-C$_{12}$)-alkoxy groups.

In one embodiment, $R^1$, $R^2$, $R^3$, $R^4$, $R^5$, $R^6$, $R^7$, $R^8$ may be selected from:
—H, —(C$_1$-C$_{12}$)-alkyl, —O—(C$_1$-C$_{12}$)-alkyl, —O—(C$_6$-C$_{20}$)-aryl, —S-alkyl and —S-aryl.

In one embodiment, $R^9$, $R^{10}$, $R^{11}$, $R^{12}$, $R^{13}$, $R^{14}$, $R^{15}$, $R^{16}$, $R^{17}$, $R^{18}$ may be selected from:
—H, —(C$_1$-C$_{12}$)-alkyl, —O—(C$_1$-C$_{12}$)-alkyl, —O—(C$_6$-C$_{20}$)-aryl, —S-alkyl, and —S-aryl.

In one embodiment, X may be selected from:
—(C$_1$-C$_{12}$)-alkyl, —(C$_6$-C$_{20}$)-aryl, —(C$_3$-C$_{12}$)-cycloalkyl.

In one embodiment, Y may be selected from:
—(C$_1$-C$_{12}$)-alkyl, —(C$_6$-C$_{20}$)-aryl, —(C$_3$-C$_{12}$)-cycloalkyl.

In one embodiment, $R^1$ and $R^8$ are not the same radical.
In one embodiment, $R^2$ and $R^7$ are not the same radical.
In one embodiment, $R^3$ and $R^6$ are not the same radical.
In one embodiment, $R^4$ and $R^5$ are not the same radical.
In one embodiment, X may be the following radical:

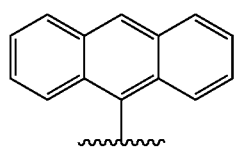

(XI)

In one embodiment, X may be the following radical:

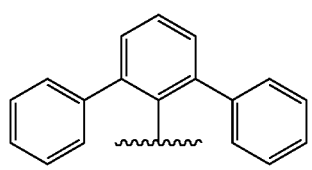

(X2)

In one embodiment, X may be the following radical:

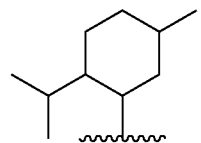

(X3)

In one embodiment, Y may be the following radical:

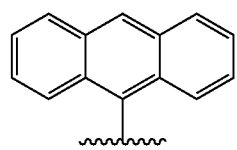

(Y1)

In one embodiment, Y may be the following radical:

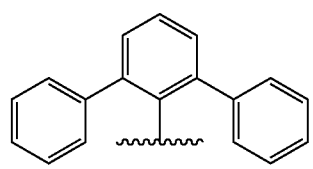

(Y2)

In one embodiment, Y may be the following radical:

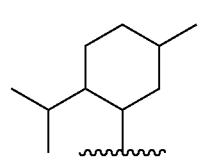

(Y3)

In one embodiment, the compound may be of structure (I).

In one embodiment, the compound may be structure (II).

In one embodiment, the compound may be one of formulae (1) to (19):

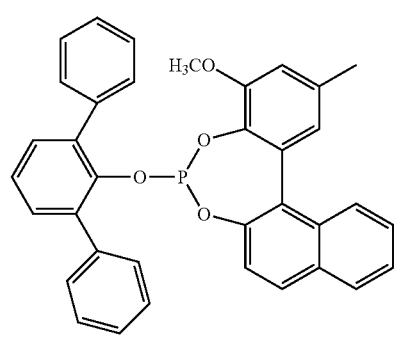

(1)

(2)
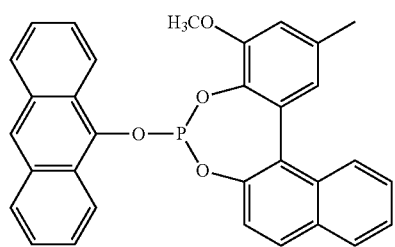
(3)
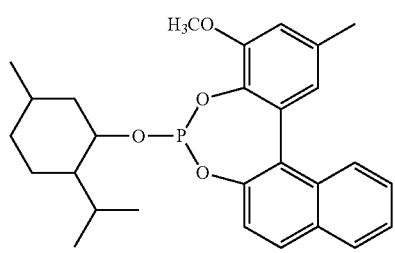
(4)
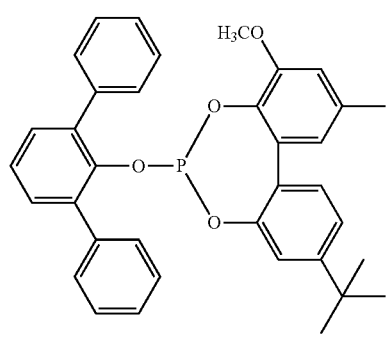
(5)
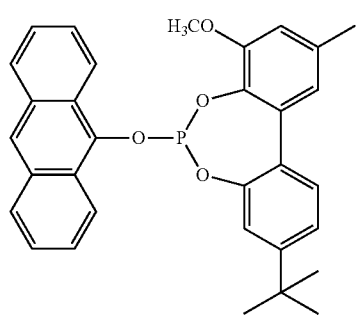
(6)
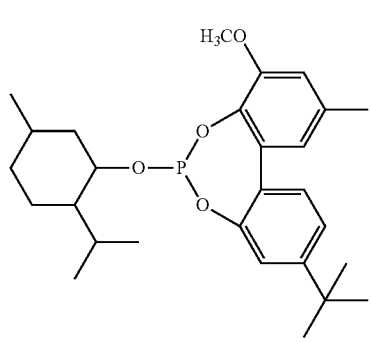
(7)
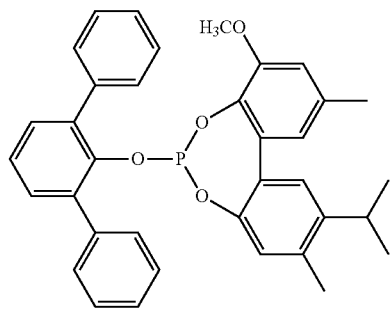
(8)
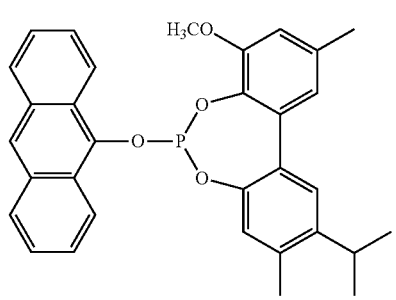
(9)
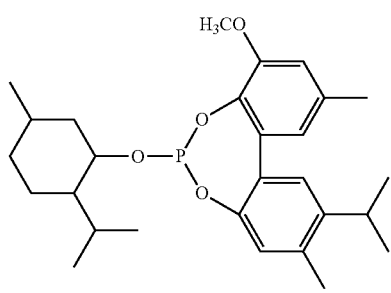
(10)
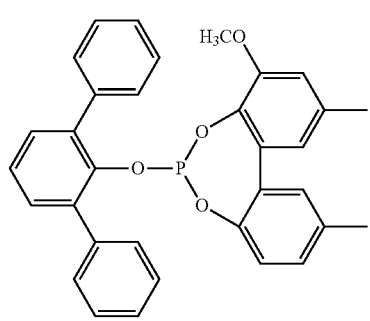
(11)
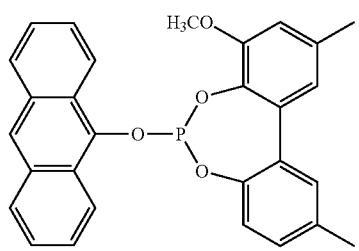

-continued

(12) 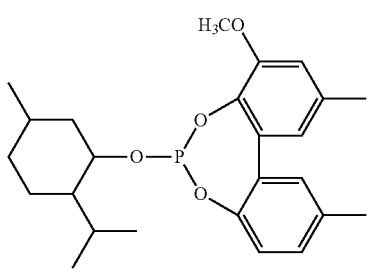

(13) 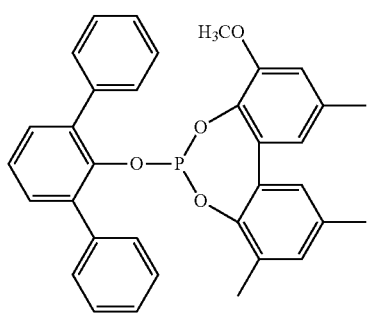

(14) 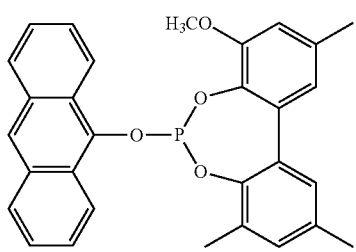

(15) 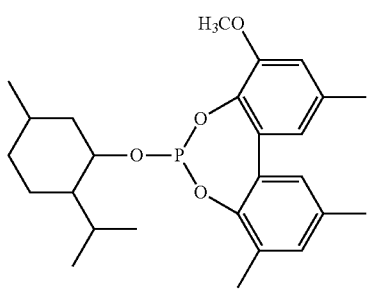

(16) 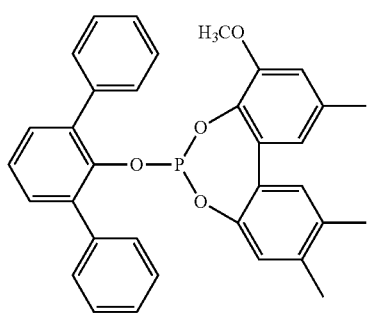

-continued

(17) 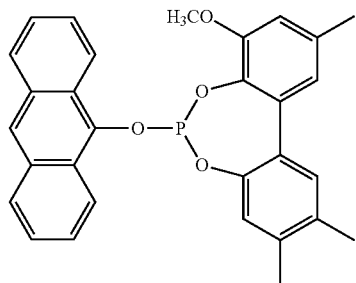

(18) 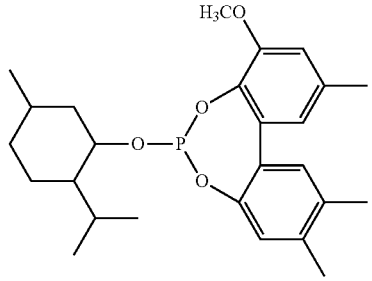

(19) 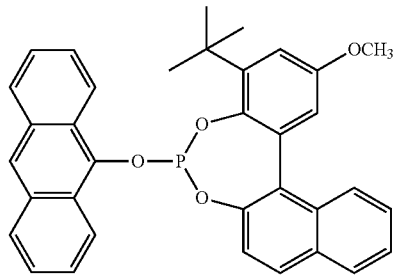

or a complex comprising one these compounds.

Another embodiment of the present invention provides a complex comprising:
a compound of structure (I) or (II), and
a metal atom selected from: Rh, Ru, Co, Ir.

In a preferred embodiment, the metal may be Rh.

In this regard, see R. Franke, D. Selent, A. Börner, "Applied Hydroformylation", Chem. Rev., 2012, DOI: 10.1021/cr3001803; p. 5688, Scheme 12 "General Method for the Preparation of a P-Modified Rh precatalyst" and references cited therein, and also P. W. N. M. van Leeuwen, in Rhodium Catalyzed Hydroformylation, P. W. N. M. van Leeuwen, C. Claver (eds.), Kluwer, Dordrecht, 2000, inter alia p. 48 ff., p. 233 ff. and references cited therein, and also K. D. Wiese and D. Obst in Top. Organomet. Chem. 2006, 18, 1-13; Springer Verlag Berlin Heidelberg 2006 p. 6 ff. and references cited therein.

In further embodiments, the present invention includes the use of the compound as a ligand in a ligand-metal complex for catalysis of a hydroformylation reaction and a process in for conversion of an olefin to an aldehyde in the presence of the ligand-metal complex.

The process may comprise at least the following operations:
a) initially charging an olefin,
b) adding a metal-ligand complex according to an embodiment of the invention,
or adding a compound according to an embodiment of the invention and a substance including a metal atom selected from: Rh, Ru, Co, Ir, c) feeding in $H_2$ and CO to obtain a reaction mixture, and d) heating the reaction mixture, to effect conversion of the olefin to an aldehyde.

In this process, process steps a) to d) may be effected in any desired sequence.

An excess of ligands may be used and each ligand may not necessarily be present bound in the form of a ligand-metal complex but may be present as free ligand in the reaction mixture.

The reaction may conducted under conventionally known conditions.

Preference is given to a temperature of 80° C. to 160° C. and a pressure of 1 bar to 300 bar.

Particular preference may given to a temperature of 100° C. to 160° C. and a pressure of 15 bar to 250 bar.

The reactant for the hydroformylation in the process of the invention may be an olefin or a mixtures of olefins, especially monoolefins having 2 to 24, preferably 3 to 16 and more preferably 3 to 12 carbon atoms, having terminal or internal C—C double bonds, for example 1-propene, 1- or 2-pentene, 2-methyl-1-butene, 2-methyl-2-butene, 3-methyl-1-butene, 1-, 2- or 3-hexene, the $C_6$ olefin mixture obtained in the dimerization of propene (dipropene), heptenes, 2- or 3-methyl-1-hexenes, octenes, 2-methyl-heptenes, 3-methylheptenes, 5-methyl-2-heptene, 6-methyl-2-heptene, 2-ethyl-1-hexene, the $C_8$ olefin mixture obtained in the dimerization of butenes (dibutene), nonenes, 2- or 3-methyloctenes, the $C_9$ olefin mixture obtained in the trimerization of propene (tripropene), decenes, 2-ethyl-1-octene, dodecenes, the $C_{12}$ olefin mixture obtained in the tetramerization or the trimerization of butenes (tetrapropene or tributene), tetradecenes, hexadecenes, the $C_{16}$ olefin mixture obtained in the tetramerization of butenes (tetrabutane), and olefin mixtures prepared by cooligomerization of olefins having different numbers of carbon atoms (preferably 2 to 4).

The invention is illustrated in detail hereinafter by working examples and a FIGURE.

Having generally described this invention, a further understanding can be obtained by reference to certain specific examples which are provided herein for purposes of illustration only, and are not intended to be limiting unless otherwise specified.

EXAMPLES

General Procedures

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Phosphorus trichloride (Aldrich) was distilled under argon before use. All preparative operations were effected in baked-out vessels. The products were characterized by means of NMR spectroscopy. Chemical shifts (δ) are reported in ppm. The $^{31}P$ NMR signals were referenced as follows: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

The recording of nuclear resonance spectra was effected on Bruker Avance 300 or Bruker Avance 400, gas chromatography analysis on Agilent GC 7890A, elemental analysis on Leco TruSpec CHNS and Varian ICP-OES 715, and ESI-TOF mass spectrometry on Thermo Electron Finnigan MAT 95-XP and Agilent 6890 N/5973 instruments.

Synthesis of Unsymmetric Biaryls

The unsymmetric biaryls were prepared by an electrochemical method by coupling two phenols or one naphthol and one phenol which differ in terms of oxidation potential. In this regard, see also B. Elsler, D. Schollmeyer, K. M. Dyballa, R. Franke, S. R. Waldvogel, "Metall- und reagensfreie hochselektive anodische Kreuzkupplung von Phenolen" [Metal- and Reagent-Free High-Selectivity Anodic Cross-Coupling of Phenols], Angew. Chem., 2014, DOI: 10.1002/ange.201400627

General Procedure:

The coupling reaction was conducted in an apparatus as shown in the FIGURE.

5 mmol of the first phenol having an oxidation potential $E_{Ox}1$ together with 15 mmol of the second phenol having an oxidation potential $E_{Ox}2$ were dissolved in 1,1,1,3,3,3-hexafluoroisopropanol (HFIP) and MeOH or in formic acid and MeOH in the amounts specified in Table 1 below. The electrolysis was galvanostatic.

The outer shell of the electrolysis cell was kept at a controlled temperature of about 10° C. with a thermostat, while the reaction mixture was stirred and heated to 50° C. with the aid of a sand bath. After the electrolysis was ended, the cell contents were transferred together with toluene to a 50 ml round-bottom flask and the solvent was removed on a rotary evaporator at 50° C., 200-70 mbar, under reduced pressure. Unconverted reactant was recovered by means of short-path distillation (100° C., $10^{-3}$ mbar).

Electrode Material
  Anode: boron-doped diamond (BDD) on Si
  Cathode: Ni mesh
Electrolysis Conditions:
  Temperature [T]: 50° C.
  Current [I]: 15 mA
  Current density [j]: 2.8 $mA/cm^2$
  Charge [Q]: 2 F/mol of deficiency component
  Terminal voltage [$U_{max}$]: 3-5 V The biaryls were synthesized by the general method described above, and in a reaction apparatus as shown in the FIGURE.

2,2'-Dihydroxy-4',5-dimethyl-5'-(methylethyl)-3-methoxybiphenyl

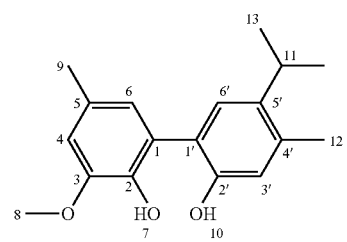 [SMILES: COc1cc(C)cc(-c2cc(C(C)C)c(C)cc2O)c1O]

0.69 g (5 mmol, 1.0 equiv.) of 4-methylguaiacol and 2.28 g (15 mmol, 3.0 equiv.) of 3-methyl-4-(methylethyl)phenol were dissolved in 33 ml of HFIP, 0.68 g of methyltriethylammonium methylsulphate (MTES) was added and the electrolyte was transferred to the electrolysis cell. After the electrolysis, the solvent and unconverted amounts of reactant were removed under reduced pressure, the crude product was purified by flash chromatography on silica gel 60 in a 9:1 eluent (cyclohexane:ethyl acetate) and the product was obtained as a colourless solid.

Yield: 716 mg (50%, 2.5 mmol)
GC (hard method, HP-5): $t_R$=14.87 min
$R_f$(CH:EA=4:1)=0.43
$m_p$=126.8° C. (recrystallized from CH)
$^1$H-NMR (600 MHz, DMSO) δ=1.17-1.12 (m, 6H, 13-H), 2.24 (m, 6H, 9-H/12-H), 3.01 (dt, 1H, 11-H), 3.79 (s, 3H, 8-H), 6.55 (s, 1H, 6-H), 6.66 (d, 1H, 6'-H), 6.73 (d, 1H, 4-H), 6.96 (s, 1H, 3'-H), 8.16 (s, 1H, 7-H), 8.84 (s, 1H, 10-H);
Couplings: $^4J_{4\text{-}H,\ 6\text{-}H}$=2.2 Hz, $^4J_{6'\text{-}H,\ 11\text{-}H}$=2.9 Hz, $^3J_{11\text{-}H,\ 13\text{-}H}$=6.8 Hz;
$^{13}$C-NMR (151 MHz, DMSO) δ=18.73, 20.80 (C-9/C-12), 23.54 (C-13), 28.10 (C-11), 55.78 (C-8), 111.23 (C-4), 117.34 (C-6'), 123.42 (C-1'), 123.49 (C-6), 126.43 (C-1), 127.36 (C-5), 127.49 (C-3'), 134.40 (C-5'), 136.62 (C-4'), 141.12 (C-2), 147.65 (C-3), 151.69 (C-2').
HRMS for $C_{18}H_{22}O_3$(ESI+) [M+Na$^+$]: calc: 309.1467. found: 309.1457.
MS (EI, GCMS): m/z (%): 286 (50) [M]$^+$., 271 (100) [M-CH$_3$.]$^+$, 244 (22) [M-C$_3$H$_6$.]$^+$.
Elemental analysis for $C_{18}H_{22}O_3$: calc: C, 75.50%; H, 7.74%. found: C, 75.01%; H, 7.70%.

2,2'-Dihydroxy-5,5'-dimethyl-3-methoxybiphenyl 1.66 g (12 mmol, 1.0 equiv.) of 4-methylguaiacol and 3.91 g (36 mmol, 3.0 equiv.) of 4methylphenol were dissolved in 65 ml of HFIP and 14 ml of MeOH, 1.63 g of MTES were added and the electrolyte was transferred to the electrolysis cell. After the electrolysis, the solvent and unconverted amounts of reactant were removed under reduced pressure, the crude product was purified by flash chromatography on silica gel 60 in a 4:1 eluent (cyclohexane:ethyl acetate) and the product was obtained as a colourless solid.

Yield: 440 mg (36%, 1.8 mmol)
GC (hard method, HP-5): $t_R$=13.56 min
$R_f$(CH:EA=4:1)=0.38
$m_p$=162.0° C. (recrystallized from CH)
$^1$H-NMR (400 MHz, DMSO) δ=2.18 (s, 3H, 9-H/11-H), 2.21 (s, 3H, 9-H/11-H), 3.76 (s, 3H, 8-H), 6.53 (s, 1H, 6-H), 6.71 (s, 1H, 4-H), 6.75 (d, 1H, 3'-H), 6.86-6.94 (m, 2H, 4'-H/6'-H), 8.53 (bs, 1H, 7-H/12-H);
Couplings: $^3J_{3'\text{-}H,\ 4'\text{-}H}$=8.4 Hz;
$^{13}$C-NMR (101 MHz, DMSO) δ=20.21, 20.77 (C-9/C-11), 55.79 (C-8), 111.36 (C-4), 115.69 (C-3'), 123.50 (C-6), 125.72 (C-1'), 126.16 (C-1), 127.20 (C-5), 127.30 (C-5'), 128.50 (C-6'), 131.83 (C-4'), 141.20 (C-2), 147.61 (C-3), 152.11 (C-2').

HRMS for $C_{15}H_{16}O_3$(ESI+) [M+Na$^+$]: calc: 267.0997. found: 267.0999.
MS (EI, GCMS): m/z (%): 244 (100) [M]$^+$., 229 (64) [M-CH$_3$.]$^+$.
Elemental analysis for $C_{15}H_{16}O_3$: calc: C, 73.75%; H, 6.60%. found: C, 73.81%; H, 6.54%.

2,2'-Dihydroxy-3-methoxy-3',5,5'-trimethylbiphenyl 0.70 g (6 mmol, 1.0 equiv.) of 4-methylguaiacol and 2.08 g (17 mmol, 3.0 equiv.) of 2,4dimethylphenol were dissolved in 27 ml of HFIP and 6 ml of MeOH, 0.68 g of MTES were added and the electrolyte was transferred to the electrolysis cell. After the electrolysis, the solvent and unconverted amounts of reactant were removed under reduced pressure, the crude product was purified by flash chromatography on silica gel 60 in a 9:1 eluent (cyclohexane:ethyl acetate) and the product was obtained as a pale yellow solid.

Yield: 663 mg (45%, 2.5 mmol)
GC (hard method, HP-5): $t_R$=13.97 min
$R_f$(CH:EA=4:1)=0.29
$m_p$=119.7° C. (recrystallized from DCM/CH)
$^1$H-NMR (400 MHz, CDCl$_3$) δ=2.34 (s, 3H, 10-H), 2.35 (s, 3H, 11-H), 2.38 (s, 3H, 9-H), 3.94 (s, 3H, 8-H), 6.16 (s, 1H, 12-H), 6.20 (s, 1H, 7-H), 6.76 (d, 1H, 4-H), 6.78 (d, 1H, 6-H), 6.98 (d, 1H, 6'-H), 7.03 (d, 1H, 4'-H);
Couplings: $^4J_{4\text{-}H,\ 6\text{-}H}$=1.7 Hz, $^4J_{4'\text{-}H,\ 6'\text{-}H}$=2.1 Hz;
$^{13}$C-NMR (101 MHz, CDCl$_3$) δ=16.51 (C-9), 20.54 (C-10), 21.20 (C-11), 56.12 (C-8), 110.92 (C-4), 123.95 (C-6), 124.13 (C-1), 124.64 (C-1'), 126.18 (C-3'), 128.82 (C-6'), 129.59 (C-5'), 130.40 (C-5), 131.40 (C-4'), 139.46 (C-2), 146.35 (C-3), 149.42 (C-2').
HRMS for $C_{18}H_{16}O_3$(ESI+) [M+Na$^+$]: calc: 281.1154. found: 281.1152.
MS (EI, GCMS): m/z (%): 242 (100) [M]$^+$., 227 (38) [M-CH$_3$.]$^+$.
Elemental analysis for $C_{16}H_{18}O_3$: calc: C, 68.31%; H, 6.45%. found: C, 68.29%; H, 6.40%.

2,2'-Dihydroxy-3-methoxy-5-methyl-4'-(dimethylethyl)biphenyl 0.69 g (5 mmol, 1.0 equiv.) of 4-methylguaiacol and 2.25 g (15 mmol, 3.0 equiv.) of 3-tert-butylphenol were dissolved in 33 ml of HFIP, 0.68 g of MTES were added and the electrolyte was transferred to the electrolysis cell. After the electrolysis, the solvent and unconverted amounts of reactant were removed under reduced pressure, the crude product was purified by flash chromatography on silica gel 60 in a 4:1 eluent (cyclohexane:ethyl acetate) and the product is obtained as a colourless solid.

Yield: 808 mg (63%, 3.1 mmol)
GC (hard method, HP-5): $t_R$=13.97 min
$R_f$(CH:EA=4:1)=0.29
$m_p$=160.3° C. (recrystallized from DCM/CH)
$^1$H-NMR (400 MHz, CDCl$_3$) δ=1.37 (s, 9H, 12-H), 2.36 (s, 3H, 9-H), 3.94 (s, 3H, 8-H), 6.25 (s, 1H, 7-H), 6.48 (s, 1H, 10-H), 6.75 (d, 1H, 6-H), 6.79 (d, 1H, 4-H), 7.08 (dd, 1H, 5'-H), 7.12 (d, 1H, 3'-H), 7.27 (d, 1H, 6'-H);
Couplings: $^4J_{4\text{-}H,\ 6\text{-}H}$=1.7 Hz; $^3J_{5'\text{-}H,\ 6'\text{-}H}$=8.0 Hz, $^4J_{3'\text{-}H,\ 5'\text{-}H}$=1.7 Hz;
$^{13}$C-NMR (101 MHz, CDCl$_3$) δ=21.24 (C-9), 31.31 (C-12), 34.58 (C-11), 56.15 (C-8), 110.79 (C-4), 114.94 (C-3'), 118.30 (C-5'), 122.37 (C-1'), 123.88 (C-1), 123.94 (C-6), 130.45 (C-6'), 130.53 (C-4'), 139.24 (C-5), 146.32 (C-3), 152.91 (C-2'), 153.13 (C-2).
HRMS for C$_{15}$H$_{16}$O$_4$(ESI+) [M+Na$^+$]: calc: 309.1467. found: 309.1466.
MS (EI, GCMS): m/z (%): 242 (100) [M]$^+$., 227 (38) [M-CH$_3$.]$^+$.
Elemental analysis for C$_{18}$H$_{22}$O$_3$: calc: 75.50%; H, 7.74%. found: C, 75.41%; H, 7.72%.

2,2'-Dihydroxy-4',5-dimethy-3-methoxylbiphenyl 0.70 g (5 mmol, 1.0 equiv.) of 4-methylguaiacol and 1.65 g (15 mmol, 3.0 equiv.) of 3methylphenol were dissolved in 33 ml of HFIP, 0.68 g of MTES were added and the electrolyte was transferred to the electrolysis cell. After the electrolysis, the solvent and unconverted amounts of reactant are removed under reduced pressure, the crude product was purified by flash chromatography on silica gel 60 in a 4:1 eluent (cyclohexane:ethyl acetate) and two cross-coupling products were obtained as colourless solids.

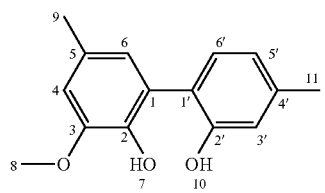

Yield: 266 mg (21%, 1.1 mmol)
GC (hard method, HP-5): $t_R$=13.72 min
$R_f$(CH:EA=4:1)=0.25
$m_p$=136.2° C. (recrystallized from DCM/CH)
$^1$H-NMR (400 MHz, CDCl$_3$) δ=2.35 (s, 3H, 9-H/11-H), 2.37 (s, 3H, 9-H/11-H), 3.94 (s, 3H, 8-H), 6.17 (s, 1H, 10-H), 6.35 (s, 1H, 2-H), 6.74 (d, 1H, 4-H), 6.76 (s, 1H, 6-H), 6.88-6.83 (m, 1H, 5'-H), 6.90 (d, 1H, 3'-H), 7.21 (d, 1H, 6'-H);
Couplings: $^4J_{4\text{-}H,\ 6\text{-}H}$=1.8 Hz, $^3J_{5'\text{-}H,\ 6'\text{-}H}$=7.7 Hz, $^4J_{3'\text{-}H,\ 5'\text{-}H}$=1.5 Hz;
$^{13}$C-NMR (101 MHz, CDCl$_3$) δ=21.11, 21.20 (C-9/C-11), 56.13 (C-8), 110.81 (C-4), 118.25 (C-3'), 121.97 (C-5'), 122.39 (C-1), 123.77 (C-1'), 123.85 (C-6), 130.50 (C-5), 130.68 (C-6'), 139.30 (C-4'), 139.54 (C-2), 146.31 (C-3), 153.33 (C-2').

HRMS for C$_{15}$H$_{16}$O$_3$(ESI+) [M+Na$^+$]: calc: 267.0997. found: 267.1006.
MS (EI, GCMS): m/z (%): 244 (100) [M]$^+$., 229 (18) [M-CH$_3$.]$^+$.
Elemental analysis for C$_{15}$H$_{16}$O$_3$: calc: C, 73.75%; H, 6.60%. found: C, 73.70%; H, 6.68%.

2,2'-Dihydroxy-3-methoxy-4'-5,5'-trimethylbiphenyl

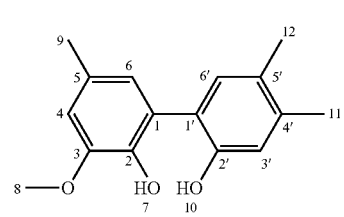

0.69 g (5 mmol, 1.0 equiv.) of 4-methylguaiacol and 1.83 g (15 mmol, 3.0 equiv.) of 3,4dimethylphenol were dissolved in 27 ml of HFIP and 6 ml of MeOH, 0.68 g of MTES were added and the electrolyte was transferred to the electrolysis cell. After the electrolysis, the solvent and unconverted amounts of reactant were removed under reduced pressure, the crude product was purified by flash chromatography on silica gel 60 in a 9:1 eluent (cyclohexane:ethyl acetate) and the product was obtained as a colourless solid.

Yield: 688 mg (52%, 2.6 mmol)
GC (hard method, HP-5): $t_R$=14.52 min
$R_f$(CH:EA=4:1)=0.29
$m_p$=152.3° C. (recrystallized from DCM/CH)
$^1$H-NMR (400 MHz, CDCl$_3$) δ=12.25 (s, 3H, 11-H), 2.28 (s, 3H, 12-H), 2.36 (s, 3H, 9-H), 3.93 (s, 3H, 8-H), 6.19 (s, 1H, 7-H), 6.25 (s, 1H, 10-H), 6.73 (d, 1H, 4-H), 6.76 (s, 1H, 6-H), 6.88 (s, 1H, 3'-H), 7.08 (s, 1H, 6'-H);
Couplings: $^4J_{4\text{-}H,\ 6\text{-}H}$=1.7 Hz;
$^{13}$C-NMR (101 MHz, CDCl$_3$) δ=18.89 (C-11), 19.60 (C-12), 21.24 (C-9), 56.14 (C-8), 110.74 (C-4), 118.93 (C-3'), 122.54 (C-1), 123.82 (C-6), 123.97 (C-1'), 129.03 (C-5), 130.46 (C-4'), 131.69 (C-6'), 137.94 (C-5'), 139.26 (C-2), 146.31 (C-3), 151.36 (C-2').
HRMS for C$_{16}$H$_{18}$O$_3$(ESI+) [M+Na$^+$]: calc: 281.1154. found: 281.1157.
MS (EI, GCMS): m/z (%): 258 (100) [M]$^+$., 243 (10) [M-CH$_3$.]$^+$.
Elemental analysis for C$_{16}$H$_{18}$O$_3$: calc: 74.39%; H, 7.02%. found: C, 74.32%; H, 7.20%.

2,2'-Dihydroxy-5'-isopropyl-3-methoxy-5-methylbiphenyl

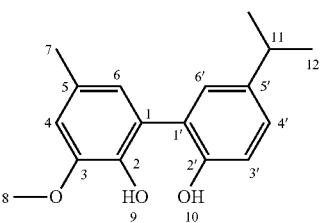 [SMILES: COc1cc(C)cc(-c2cc(C(C)C)ccc2O)c1O]

0.69 g (5 mmol, 1.0 equiv.) of 4-methylguaiacol and 2.05 g (15 mmol, 3.0 equiv.) of 4isopropylphenol were dissolved in 27 ml of HFIP and 6 ml of MeOH, 0.68 g of MTES were added and the electrolyte was transferred to the electrolysis cell. After the electrolysis, the solvent and unconverted amounts of reactant were removed under reduced pressure, the crude product was purified by flash chromatography on silica gel 60 in a 4:1 eluent (cyclohexane:ethyl acetate) and the product was obtained as a brownish oil.

Yield: 0.53 g (39%, 1.9 mmol)

GC (hard method, HP-5): $t_R$=14.23 min $R_f$(CH:EA=4:1)=0.30

$^1$H-NMR (400 MHz, CDCl$_3$) δ=1.27 (m, 6H), 2.36 (s, 3H), 2.91 (dt, J=13.8, 6.9, 6.9 Hz, 1H), 3.94 (s, 3H), 6.13-6.27 (m, 2H), 6.82-6.65 (m, 1H), 6.25 (m, 2H), 6.75 (s, 1H), 6.77 (s, 1H), 6.99 (d, J=8.1 Hz, 1H), 7.19-7.12 (m, 2H);

$^{13}$C-NMR (101 MHz, CDCl$_3$) δ=21.25, 24.27, 33.40, 56.18, 110.92, 117.60, 123.91, 124.23, 125.07, 127.29, 128.80, 130.57, 139.29, 141.42, 146.31, 151.51.

HRMS for C$_{17}$H$_{20}$O$_3$(ESI+) [M+Na$^+$]: calc: 295.1310. found: 295.1297.

MS (EI, GCMS): m/z (%): 272 (80) [M]$^+$., 257 (100) [M-CH$_3$.]$^+$.

2,2'-Dihydroxy-3-methoxy-5-methyl-5'-tert-butylbiphenyl

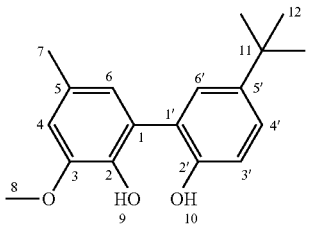 [SMILES: COc1cc(C)cc(-c2cc(C(C)(C)C)ccc2O)c1O]

0.69 g (5 mmol, 1.0 equiv.) of 4-methylguaiacol and 2.26 g (15 mmol, 3.0 equiv.) of 4-tert-butylphenol were dissolved in 27 ml of HFIP and 6 ml of MeOH, 0.68 g of MTES was added and the electrolyte was transferred to the electrolysis cell. After the electrolysis, the solvent and unconverted amounts of reactant were removed under reduced pressure, the crude product was purified by flash chromatography on silica gel 60 in a 4:1 eluent (cyclohexane:ethyl acetate) and the product was obtained as a yellowish oil.

Yield: 0.48 g (34%, 1.7 mmol)

GC (hard method, HP-5): $t_R$=14.52 min $R_f$(CH:EA=4:1)=0.24

$^1$H-NMR (400 MHz, CDCl$_3$) δ=1.34 (s, 9H), 2.37 (s, 3H), 3.94 (s, 3H), 6.17 (s, 1H), 6.24 (s, 1H), 6.75 (s, 1H), 6.77 (s, 1H), 6.99 (d, J=8.4 Hz, 1H), 7.31-7.29 (m, 1H), 7.33 (dd, J=8.4, 2.5 Hz, 1H).

$^{13}$C-NMR (101 MHz, CDCl$_3$) δ=21.28, 31.61, 34.20, 56.18, 110.91, 117.25, 123.92, 124.41, 124.63, 126.38, 127.78, 130.58, 139.32, 143.70, 146.32, 151.22.

HRMS for C$_{18}$H$_{22}$O$_3$(ESI+) [M+Na$^+$]: calc: 309.1467. found: 309.1476.

MS (EI, GCMS): m/z (%): 286 (28) [M]$^+$., 271 (100) [M-CH$_3$.]$^+$.

2,2'-Dihydroxy-3',5'-di-tert-butyl-5-methyl-3-methoxybiphenyl

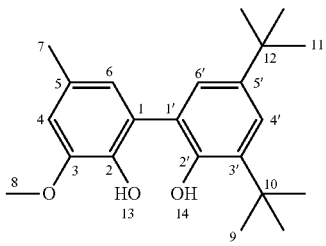 [SMILES: COc1cc(C)cc(-c2cc(C(C)(C)C)cc(C(C)(C)C)c2O)c1O]

0.69 g (5 mmol, 1.0 equiv.) of 4-methylguaiacol and 3.12 g (15 mmol, 3.0 equiv.) of 2,4-di-tert-butylphenol were dissolved in 27 ml of HFIP and 6 ml of MeOH, 0.68 g of MTES was added and the electrolyte was transferred to the electrolysis cell. After the electrolysis, the solvent and unconverted amounts of reactant were removed under reduced pressure, the crude product was purified by flash chromatography on silica gel 60 in a 9:1 eluent (cyclohexane:ethyl acetate) and the product was obtained as a colourless solid.

Yield: 0.41 g (24%, 1.2 mmol)

GC (hard method, HP-5): $t_R$=15.15 min $R_f$(CH:EA=9:1)=0.35

$m_p$=120.2° C. (recrystallized in n-pentane)

$^1$H-NMR (400 MHz, CDCl$_3$) δ=1.36 (s, 9H), 1.50 (s, 9H), 2.38 (s, 3H), 3.96 (s, 3H), 6.00 (s, 1H), 6.05 (s, 1H), 6.77 (s, 1H), 7.16 (d, J=2.5 Hz, 1H), 7.39 (d, J=2.5 Hz, 1H).

$^{13}$C-NMR (101 MHz, CDCl$_3$) δ=21.23, 29.88, 31.69, 34.40, 35.23, 56.17, 111.03, 123.96, 124.17, 125.09, 125.50, 130.42, 136.73, 139.72, 142.36, 146.45, 149.82.

MS (EI, GCMS): m/z (%): 342 (22) [M]$^+$., 327 (100) [M-CH$_3$.]$^+$.

2,2'-Dihydroxy-3',5-dimethyl-3-methoxy-5'-tert-butylbiphenyl

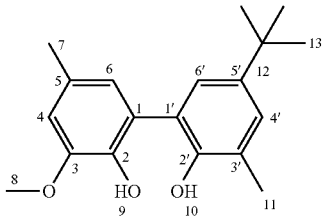 [SMILES: COc1cc(C)cc(-c2cc(C(C)(C)C)cc(C)c2O)c1O]

0.69 g (5 mmol, 1.0 equiv.) of 4-methylguaiacol and 2.47 g (15 mmol, 3.0 equiv.) of 2-methyl-4-tert-butylphenol were dissolved in 27 ml of HFIP and 6 ml of MeOH, 0.68 g of MTES was added and the electrolyte was transferred to the electrolysis cell. After the electrolysis, the solvent and unconverted amounts of reactant were removed under reduced pressure, the crude product was purified by flash chromatography on silica gel 60 in a 4:1 eluent (cyclohexane:ethyl acetate) and the product was obtained as a yellowish oil.

Yield: 0.69 g (46%, 2.3 mmol)

GC (hard method, HP-5): $t_R$=14.79 min $R_f$(CH:EA=4:1)=0.33

¹H-NMR (400 MHz, CDCl₃) δ=1.37 (s, 9H), 2.39 (d, J=2.4 Hz, 6H), 3.94 (s, 3H), 6.15 (s, 1H), 6.17 (s, 1H), 6.77 (s, 1H), 6.79 (s, 1H), 7.17 (d, J=2.5 Hz, 1H), 7.24 (d, J=2.4 Hz, 1H);

¹³C-NMR (101 MHz, CDCl₃) δ=16.90, 21.28, 31.67, 34.12, 56.16, 110.94, 124.02, 124.17, 124.59, 125.41, 125.65, 127.86, 130.47, 139.50, 143.07, 146.40, 149.41.

MS (EI, GCMS): m/z (%): 300 (18) [M]⁺., 285 (100) [M-CH₃.]⁺.

2,2'-Dihydroxy-3-methoxy-5-methyl-5'-(1-methyl-ethyl)biphenyl

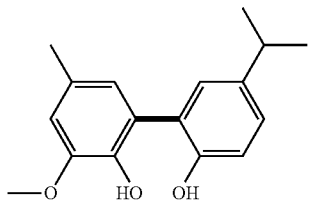

0.69 g (5 mmol, 1.0 eq.) of 4-methylguaiacol and 2.05 g (15 mmol, 3.0 eq.) of 4-isopropylphenol and 0.68 g of MTES in 27 ml of HFIP+6 ml of MeOH were added to MTES and the electrolyte was transferred to the electrolysis cell. After the electrolysis, the solvent and unconverted amounts of reactant were removed under reduced pressure, the crude product was purified by flash chromatography on silica gel 60 in a 4:1 eluent (cyclohexane:ethyl acetate) and the product was obtained as a brownish oil.

Yield: 39%, 527 mg, 1.9 mmol.

$R_f$(cyclohexane:ethyl acetate=4:1)=0.30;

¹H NMR (400 MHz, CDCl₃) δ=1.27 (m, 6H), 2.36 (s, 3H), 2.91 (sept, J=6.9 Hz, 1H), 3.94 (s, 3H), 6.13-6.27 (m, 2H), 6.65-6.82 (m, 2H), 6.99 (d, J=8.1 Hz, 1H), 7.12-7.19 (m, 2H);

¹³C NMR (101 MHz, CDCl₃) δ=21.37, 24.39, 33.53, 56.31, 111.04, 117.73, 124.04, 124.36, 125.20, 127.42, 128.93, 130.70, 139.42, 141.55, 146.44, 151.64.

HRMS for C₁₇H₂₀O₃(ESI+) [M+Na⁺]: calculated: 295.1310. measured: 295.1297.

MS (EI, GCMS): m/z (%): 272 (80) [M]⁺., 257 (100) [M-CH₃.]⁺.

2,2'-Dihydroxy-3-methoxy-5-methyl-4'-(methyl-ethyl)biphenyl

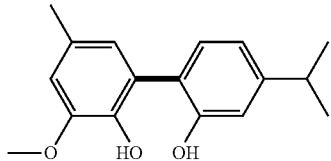

0.69 g (5 mmol, 1.0 eq.) of 4-methylguaiacol and 2.065 g (15 mmol, 3.0 eq.) of 3-isopropylphenol and 0.68 g of MTES were dissolved in 33 ml of HFIP and the electrolyte was transferred to the electrolysis cell. After the electrolysis, the solvent and unconverted amounts of reactant were removed under reduced pressure, the crude product was purified by flash chromatography on silica gel 60 in a 4:1 eluent (cyclohexane:ethyl acetate) and the product is obtained as a brownish oil (yield: 52%, 705 mg, 2.6 mmol).

$R_f$(cyclohexane:ethyl acetate=4:1)=0.29.

¹H NMR (400 MHz, CDCl₃) δ=1H NMR (400 MHz, CDCl3) δ 1.27 (s, 3H), 1.29 (s, 3H), 2.34 (s, 3H), 2.91 (sept, J=7.0 Hz, 1H), 3.94 (s, 3H), 6.15 (s, 1H), 6.35 (s, 1H), 6.73 (d, J=1.8 Hz, 1H), 6.75-6.77 (m, 1H), 6.90 (dd, J=7.9 Hz, 1.8 Hz, 1H), 6.94 (d, J=1.7 Hz, 1H), 7.23 (d, J=7.8 Hz, 1H).

¹³C NMR (101 MHz, CDCl₃) δ=¹³C NMR (101 MHz, CDCl₃) δ 21.36, 24.02, 33.92, 56.30, 77.16, 110.91, 115.77, 119.56, 122.81, 124.00, 124.08, 130.65, 130.84, 139.38, 146.43, 150.72, 153.54.

HRMS for C₁₇H₂₀O₃(ESI+) [M+Na⁺]: calculated: 295.1310. measured: 295.1305; MS (EI, GCMS): m/z (%): 272 (100) [M]⁺., 257 (50) [M-CH₃⁻.]⁺.]⁺. Elemental analysis for C₁₇H₂₀O₃: calculated 74.97%; H, 7.40%. measured: C, 75.05%; H, 7.36%.

2,2'-Dihydroxy-4',5-dimethyl-3-methoxybiphenyl

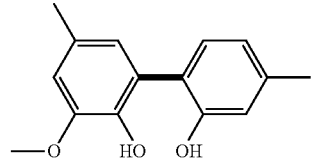

0.28 g (2 mmol, 1.0 eq.) of 4-methylguaiacol, 1.22 g (6 mmol, 3.0 eq.) of 3-methylphenol and 0.77 g of MTBS were dissolved in 25 ml of HFIP and the electrolyte was transferred to the beaker-type electrolysis cell. After the electrolysis, the solvent and unconverted amounts of reactant were removed under reduced pressure, the crude product was purified by flash chromatography on silica gel 60 in a 4:1 eluent (cyclohexane:ethyl acetate) and this led to the two cross-coupling products as a colourless and viscous oil.

Yield: 21%, 266 mg, 1.1 mmol; $R_f$(cyclohexane:ethyl acetate=4:1)=0.25; $m_p$=136.2° C. (crystallized from dichloromethane/cyclohexane);

¹H NMR (400 MHz, CDCl₃) δ=2.35 (s, 3H), 2.37 (s, 3H), 3.94 (s, 3H), 6.17 (s, 1H), 6.35 (s, 1H), 6.74 (d, J=1.8 Hz, 1H), 6.76 (s, 1H), 6.88-6.83 (m, 1H), 6.90 (d, 1H, J=1.5 Hz), 7.21 (d, 1H, J=7.7 Hz);

¹³C NMR (101 MHz, CDCl₃) δ=21.11, 21.20 56.13, 110.81, 118.25, 121.97, 122.39, 123.77, 123.85, 130.50, 130.68, 139.30, 139.54, 146.31, 153.33.

HRMS for C₁₅H₁₆O₃(ESI+) [M+Na⁺]: calculated: 267.0997. measured: 267.1006; MS (EI, GCMS): m/z (%): 244 (100) [M]⁺., 229 (18) [M-CH₃.]⁺. Elemental analysis for C₁₅H₁₆O₃: calculated C, 73.75%; H, 6.60%. measured: C, 73.70%; H, 6.68%.

2,2'-Dihydroxy-5,5'-dimethyl-3'-(1,1-dimethylethyl)-3-methoxybiphenyl

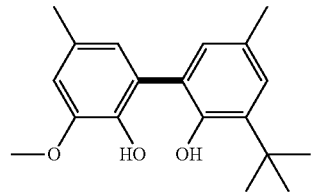

0.69 g (5 mmol, 1.0 eq.) of 4-methylguaiacol, 2.47 g (15 mmol, 3.0 eq.) of 4-methyl-2-tert-butylphenol and 0.68 g of MTES were dissolved in 27 ml of HFIP+6 ml of MeOH and the electrolyte was transferred to the electrolysis cell. After the electrolysis, the solvent and unconverted amounts of reactant were removed under reduced pressure, the crude product was purified by flash chromatography on silica gel 60 in a 4:1 eluent (cyclohexane:ethyl acetate) and the product is obtained as a yellow oil (yield: 36%, 545 mg, 1.8 mmol).

$R_f$(cyclohexane:ethyl acetate=9:1)=0.36;

$^1H$ NMR (400 MHz, $CDCl_3$) δ=1.46 (s, 9H), 2.34 (m, 6H), 3.93 (s, 3H), 5.99 (s, 1H), 6.01 (s, 1H), 6.74 (s, 2H), 6.96 (d, J=1.9 Hz, 1H), 7.14 (d, J=1.9 Hz, 1H);

$^{13}C$ NMR (101 MHz, $CDCl_3$) δ=21.05, 21.32, 29.96, 35.05, 56.30, 77.16, 111.21, 124.18, 124.24, 125.92, 127.67, 129.15, 129.22, 130.51, 137.57, 139.87, 146.57, 150.10.

HRMS for $C_{22}H_{30}O_3$(ESI+) [M+Na$^+$]: calculated: 323.1623. measured: 323.1618; MS (EI, GCMS): m/z (%): 300 (100) [M]$^+$., 285 (100) [M-$CH_3$.]$^+$.

1-(2-Hydroxy-3-methoxy-5-methylphenyl)-2-naphthol

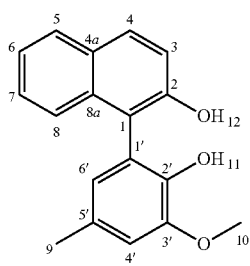

The electrolysis was conducted according to the general procedure in an undivided flange cell with a BDD anode. For this purpose, 0.78 g (5 mmol, 1.0 equiv.) of 2-naphthol and 2.18 g (15 mmol, 3.0 equiv.) of 4-methylguaiacol are dissolved in 27 ml of HFIP and 6 ml of MeOH, 0.68 g of MTES was added and the electrolyte was transferred to the electrolysis cell. The solvent and unconverted amounts of reactant were removed under reduced pressure after the electrolysis, the crude product is purified by flash chromatography on silica gel 60 in a 4:1 eluent (CH:EA) and a product mixture was obtained. A second "flash chromatography" in dichloromethane enables a separation of the two components as a pale red crystalline main product and a colourless crystalline by-product.

Yield: 899 mg (61%, 3.2 mmol)

GC (hard method, HP-5): $t_R$=15.77 min $R_f$(CH:EA=4:1)=0.36, $R_f$(DCM)=0.36

$m_p$=145.5° C. (recrystallized from DCM/CH)

$^1H$-NMR (400 MHz, $CDCl_3$) δ=2.39 (s, 3H, 9-H), 3.96 (s, 3H, 10-H), 5.47-5.52 (m, 1H, 12-H), 5.65-5.69 (m, 1H, 11-H), 6.75 (d, 1H, 6'-H), 6.85 (d, 1H, 4'-H), 7.32 (dd, 1H, 3-H), 7.34-7.43 (m, 2H, 6-H/7-H), 7.51 (d, 1H, 8-H), 7.83 (s, 1H, 5-H), 7.85 (d, 1H, 4-H);

Couplings: $^3J_{3-H, 4-H}$=9.0 Hz, $^3J_{7-H, 8-H}$=8.3 Hz, $^4J_{4'-H, 6'-H}$=1.8 Hz;

$^{13}C$-NMR (101 MHz, $CDCl_3$) δ=21.22 (C-9), 56.08 (C-10), 112.06 (C-4'), 116.62 (C-1), 117.81 (C-3), 119.33 (C-1'), 123.36 (C-6/C-7), 124.42 (C-6'), 124.86 (C-8), 126.48 (C-6/C-7), 128.15 (C-4), 129.18 (C-4a), 129.83 (C-5), 130.36 (C-5'), 133.16 (C-8a), 141.72 (C-2'), 147.24 (C-3'), 150.84 (C-2).

HRMS for $C_{18}H_{16}O_3$(ESI+) [M+Na$^+$]: calc: 303.0997. found: 303.1003.

MS (EI, GCMS): m/z (%): 280 (100) [M]$^+$., 265 (12) [M-$CH_3$.]$^+$., 249 (12) [M-$OCH_3$.]$^+$.

Elemental analysis for $C_{18}H_{16}O_3$: calc: C, 77.12%; H, 5.75%. found: C, 76.96%; H, 5.82%.

1-(3-(Dimethylethyl)-2-hydroxy-5-methoxyphenyl)-2-naphthol

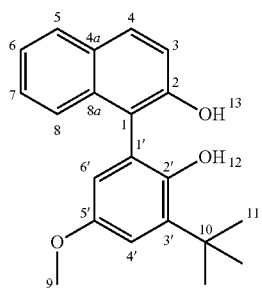

The electrolysis was conducted according to general procedure 1 in an undivided flange cell with a BDD anode. For this purpose, 0.72 g (5 mmol, 1.0 equiv.) of 2-naphthol and 2.77 g (15 mmol, 3.0 equiv.) of 2-(dimethylethyl)-4-methoxyphenol were dissolved in 27 ml of HFIP and 6 ml of MeOH, 0.68 g of MTES was added and the electrolyte was transferred to the electrolysis cell. The solvent and unconverted amounts of reactant are removed under reduced pressure after the electrolysis, the crude product was purified by flash chromatography on silica gel 60 in a 9:1 eluent (CH:EA) and the product was obtained as a colourless solid.

Yield: 1.05 g (63%, 3.2 mmol)

GC (hard method, HP-5): $t_R$=15.75 min $R_f$(CH:EA=4:1)=0.43

$m_p$=139.9° C. (recrystallized from DCM/CH)

$^1H$-NMR (400 MHz, $CDCl_3$) δ=1.46 (s, 9H, 11-H), 3.77 (s, 3H, 9-H), 4.72 (s, 1H, 2'-H), 5.36 (s, 1H, 2-H), 6.63 (d, 1H, 6'-H), 7.08 (d, 1H, 4'-H), 7.32 (d 1H, 3-H), 7.50-7.35 (m, 3H, 6-H/7-H/8-H), 7.87-7.83 (m, 1H, 5-H), 7.89 (d, 1H, 4-H);

Couplings: $^3J_{3-H, 4-H}$=8.9 Hz; $^4J_{4'-H, 6'-H}$=3.1 Hz;

$^{13}C$-NMR (101 MHz, $CDCl_3$) δ=29.41 (C-1'), 35.19 (C-10), 55.68 (C-9), 111.95 (C-6'), 114.18 (C-1), 115.87 (C-4'), 117.63 (C-3), 119.16 (C-1'), 123.89, 124.15 (C-6/C-8), 127.38 (C-7), 128.31 (C-5), 129.19 (C-4a), 130.97 (C-4), 132.99 (C-8a), 139.05 (C-3'), 146.93 (C-2'), 151.94 (C-2), 153.41 (C-5').

HRMS for $C_{21}H_{22}O_3$(ESI+) [M+Na$^+$]: calc: 345.1467. found: 345.1465.

MS (EI, GCMS): m/z (%): 322 (100) [M]$^+$., 307 (38) [M-$CH_3$.]$^+$.

Elemental analysis for $C_{21}H_{22}O_3$: calc: 78.23%; H, 6.88%. found: C, 78.18%; H, 6.82%.

Synthesis of the Chlorophosphites 2,6-Diphenylphenoxydichlorophosphine was prepared according to W. Maringgele, A. Meler, Phosphorus, Sulfur and Silicon, 1994, 90, 235-241.

Dichloro((−)-menthyloxy)phosphine was prepared according to T. Imamoto, T. Yoshizawa, K. Hirose, Y. Wada, H. Masuda, K. Yamaguchi, H. Seki, Heteroatom Chemistry, 1995, 6, 99-104.

(Anthracen-9-yloxy)dichlorophosphine was prepared according to the following synthesis method:

A mixture of anthrone (2.03 g; 10.44 mmol) and triethylamine (2 ml) in THF (80 ml) was added dropwise to a stirred solution of PCl$_3$ (5.16 g; 37.6 mmol) in THF (25 ml) at 10° C. within 90 min. After being left to stand overnight, the mixture was filtered, the filtrate was concentrated to dryness under reduced pressure and the residue obtained was taken up in toluene (50 ml). The mixture was filtered again, the solvent was removed under reduced pressure and the yellow residue was dried at 50° C./0.1 mbar. Subsequently, the solid obtained was stirred with hexane (30 ml) at room temperature overnight. The mixture was filtered and the filtercake was washed with hexane (3×20 ml). Yield: 2.27 g (73%). $^{31}$P NMR (CD$_2$Cl$_2$):

Synthesis of the Ligands 6-([1,1':3',1''-Terphenyl]-2'-yloxy)-4-methoxy-2-methylbenzo[d]naphtho[1,2-f][1,3,2]dioxaphosphepine

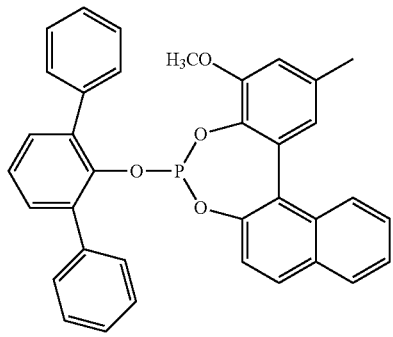

(1)

To a solution of 1-(2-hydroxy-3-methoxy-5-methylphenyl)naphthalen-2-ol (0.468 g; 1.670 mmol) in toluene (12 ml) was added triethylamine (1.548 g; 15.296 mmol), and the mixture was cooled to 0° C. To this mixture was added dropwise a solution of 2,6-diphenylphenoxydichlorophosphine (0.580 g; 1.670 mmol) in toluene (3 ml). The reaction mixture was stirred overnight at room temperature and for 2 h at 70° C. The mixture was filtered through silica gel and the filtrate was concentrated to dryness under reduced pressure. The resulting solid was dried at 50° C./0.1 mbar and purified by column chromatography (hexane/dichloromethane, 1:2, R$_f$=0.5). Yield: 0.760 g (1.370 mmol; 97%).

Elemental analysis (calc. for C$_{36}$H$_{27}$O$_4$P=554.58 g/mol) C, 78.04 (77.97); H, 4.94 (4.91); P, 5.53 (5.58)%.

$^{31}$P NMR (CD$_2$Cl$_2$): 145.5; 149.4 ppm.

$^1$H NMR (CD$_2$Cl$_2$): 2.39-2.54 (2s, 3H); 3.77-3.95 (2s, 3H); 6.16 (m, 1H, H$_{arom}$); 6.79 (m, 1H, H$_{arom}$); 6.91-6.94 (m, 1H, H$_{arom}$); 7.29-7.40 (m, 2H, H$_{arom}$); 7.40-7.46 (m, 7H, H$_{arom}$); 7.50-7.55 (m, 2H, H$_{arom}$); 7.55-7.65 (m, 5H, H$_{arom}$); 7.90-7.95 (m, 1H, H$_{arom}$); 8.05-8.11 (m, 1H, H$_{arom}$) ppm.

$^{13}$C NMR (CD$_2$Cl$_2$): 21.6; 56.1; 112.9; 121.8; 124.3; 125.2; 126.0; 126.8; 127.7; 128.4; 128.6; 128.8; 129.5; 130.6; 131.3; 131.8; 132.1; 135.0; 135.6; 136.5 (d, J$_{CP}$=4.3 Hz); 138.9; 146.3 (d, J$_{CP}$=6.8 Hz); 147.3 (d, J$_{CP}$=6.6 Hz); 152.4 (d, J$_{CP}$=2.5 Hz) ppm.

6-(Anthracen-9-yloxy)-4-methoxy-2-methylbenzo[d]naphtho[1,2-f][1,3,2]dioxaphosphepine

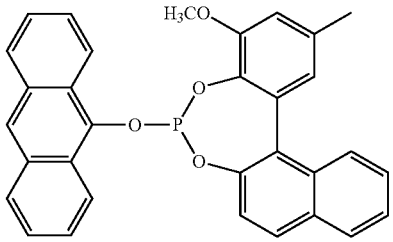

(2)

To a solution of 1-(2-hydroxy-3-methoxy-5-methylphenyl)naphthalen-2-ol (0.448 g; 1.598 mmol) in THF (8 ml) was added pyridine (0.284 g; 3.596 mmol). A solution of (anthracen-9-yloxy)dichlorophosphine (0.472 g; 1.598 mmol) in THF (6 ml) was then added dropwise at 0° C. The reaction mixture was stirred overnight, filtrate was concentrated to dryness under vacuum. The residue obtained was recrystallized from hot dichloromethane (13 ml). Yield: 0.302 g (0.601 mmol; 38%).

Elemental analysis (calc. for C$_{32}$H$_{23}$O$_4$P=502.50 g/mol) C, 76.38 (76.49); H, 4.68 (4.61); P, 6.15 (6.16)%.

$^{31}$P-NMR (THF-d$_8$): 147.3; 152.7 ppm.

$^1$H-NMR (THF-d$_8$): 29-2.31 (2s, 3H); 3.77-3.87 (2s, 3H); 6.92 (m, 1H, H$_{arom}$); 7.01 (m, 1H, H$_{arom}$); 7.34-7.46 (m, 7H, H$_{arom}$); 7.47-7.58 (m, 1H, H$_{arom}$); 7.81-7.95 (m, 4H, H$_{arom}$); 8.11 (m, 1H, H$_{arom}$); 8.25 (m, 1H, H$_{arom}$); 8.47 (m, 1H, H$_{arom}$); 8.74 (m, 1H, H$_{arom}$) ppm. $^{13}$C-NMR (THF-d$_8$): 20.6; 20.7; 55.2; 55.5; 112.4; 112.8; 121.4; 121.6; 122.6; 123.0; 123.0; 123.8; 124.0; 124.6; 124.6; 124.9; 125.1; 125.5; 125.5; 125.6; 125.7; 125.7; 126.2; 126.2; 126.6; 126.7; 127.9; 128.0; 128.4; 128.4; 128.5; 128.5; 129.5; 130.0; 130.2 (d, J$_{CP}$=4.3 Hz); 132.0; 132.3; 132.5; 134.0; 134.8; 135.7; 137.6; 143.2 (d, J$_{CP}$=7.7 Hz); 143.5 (d, J$_{CP}$=8.3 Hz); 145.8 (d, J$_{CP}$=2.8 Hz); 147.2 (d, J$_{CP}$=6.7 Hz); 152.2; 152.5 (d, J$_{CP}$=2.6 Hz) ppm.

6-((2-Isopropyl-5-methylcyclohexyl)oxy)-4-methoxy-2-methylbenzo[d]naphtho[1,2-f][1,3,2]dioxaphosphepine

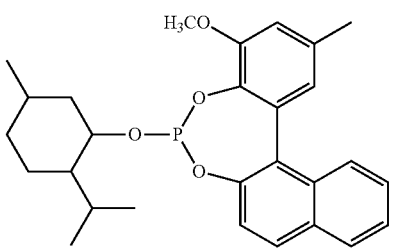

(3)

To a stirred suspension of 1-(2-hydroxy-3-methoxy-5-methylphenyl)naphthalen-2-ol (0.654 g; 2.33 mmol) in toluene (16 ml) was added triethylamine (2.17 g; 21.41 mmol) and the resulting mixture added dropwise at 0° C. to a solution of dichloro((−)-menthyloxy)phosphine (0.597 g; 2.33 mmol) in toluene (15 ml). The reaction mixture was stirred at room temperature overnight and then at 70° C. for 2 h. The mixture was filtered and the filtrate was concentrated to dryness under reduced pressure. Yield: 0.859 g (1.849 mmol; 79%).

Elemental analysis (calc. for $C_{28}H_{33}O_4P$=464.51 g/mol) C, 72.38 (72.39); H, 7.43 (7.16) %. $^{31}$P-NMR ($CD_2Cl_2$): 152.1; 154.7; 155.1; 158.5 ppm.

$^1$H-NMR ($CD_2Cl_2$): 85-1.08 (m, 10H); 1.08-1.64 (m, 4H); 1.65-1.81 (m, 2H); 2.09-2.38 (m, 2H); 2.47 (s, 3H); 3.93-3.98 (m, 3H); 4.12-4.32 (m, 1H); 6.92 (m, 1H, $H_{arom}$); 7.04-7.07 (m, 1H, $H_{arom}$); 7.26-7.34 (m, 1H, $H_{arom}$); 7.52 (m, 2H, $H_{arom}$); 7.88-7.96 (m, 2H, $H_{arom}$); 8.14-8.20 (m, 1H, $H_{arom}$) ppm.

6-([1,1':3',1''-Terphenyl]-2'-yloxy)-9-(tert-butyl)-4-methoxy-2-methyldibenzo[d,f][1,3,2]dioxaphosphepine (4)

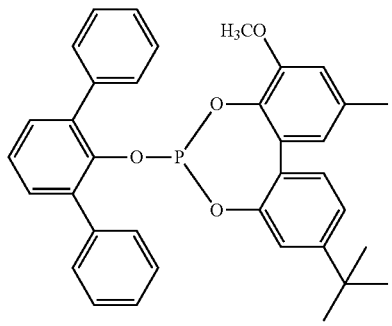

To a stirred solution of 4'-(tert-butyl)-3-methoxy-5-methyl-[1,1'-biphenyl]-2,2'-diol (0.479 g; 1.67 mmol) in toluene (12 ml) was added triethylamine (1.550 g; 15.32 mmol) and the mixture cooled to 0° C. A solution of 2,6-diphenylphenoxydichlorophosphine (0.581 g; 1.673 mmol) in toluene (3 ml) was added dropwise. The reaction mixture was stirred overnight and then filtered. The filtrate was concentrated to dryness under vacuum and the residue obtained dried at 50° C./0.1 mbar. Yield: 0.890 g (1.588 mmol; 96%).

Elemental analysis (calc. for $C_{36}H_{33}O_4P$=560.63 g/mol) C, 77.07 (77.13); H, 5.96 (5.93); P, 5.62 (5.52)%.

$^{31}$P-NMR ($CD_2Cl_2$): 144.5 ppm.

$^1$H-NMR ($CD_2Cl_2$): 41 (s, 9H); 3.82 (s, 3H); 6.81 (m, 3H, $H_{arom}$); 7.21-7.64 (m, 15H, $H_{arom}$) ppm.

$^{13}$C-NMR ($CD_2Cl_2$): 21.7; 31.5; 35.0; 56.4; 112.9; 119.3; 121.5; 122.3; 125.0; 125.7; 127.7; 128.4; 128.6; 129.4; 130.7; 131.1; 132.3 (d, $J_{CP}$=3.8 Hz); 135.5; 136.3 (d, $J_{CP}$=3.5 Hz); 138.9; 146.9 (d, $J_{CP}$=4.0 Hz); 149.8 (d, $J_{CP}$=8.1 Hz); 151.9; 153.1 ppm.

6-(Anthracen-9-yloxy)-9-(tert-butyl)-4-methoxy-2-methyldibenzo[d,f][1,3,2]dioxaphosphepine (5)

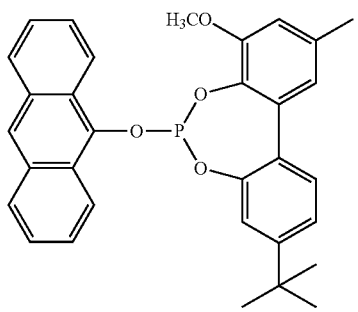

To a stirred suspension of 4'-(tert-butyl)-3-methoxy-5-methyl-[1,1'-biphenyl]-2,2'-diol (0.703 g; 2.46 mmol) in toluene (7 ml) was added triethylamine (2.277 g; 22.50 mmol) and this mixture added dropwise at 0° C. to a solution of (anthracen-9-yloxy)dichlorophosphine (0.725 g; 2.46 mmol) in toluene (13 ml). The reaction mixture was stirred overnight and then filtered. The filtrate was concentrated to dryness under vacuum and the resulting residue recrystallized from toluene (2 ml). Yield: 0.320 g (0.630 mmol; 26%).

Elemental analysis (calc. for $C_{32}H_{29}O_4P$=508.55 g/mol) C, 75.48 (75.58); H, 5.86 (5.75); P, 6.03 (6.09)%.

$^{31}$P-NMR ($CD_2Cl_2$): 148.4 ppm.

$^1$H-NMR ($CD_2Cl_2$): 44 (s, 9H); 2.49 (m, 3H); 4.00 (s, 3H); 6.94-7.04 (m, 2H, $H_{arom}$); 7.46 (m, 2H, $H_{arom}$); 7.56-7.69 (m, 5H, $H_{arom}$); 8.10 (m, 2H, $H_{arom}$); 8.39 (m, 1H, $H_{arom}$); 8.78 (m, 2H, $H_{arom}$) ppm.

$^{13}$C-NMR ($CD_2Cl_2$): 21.7; 31.3; 31.4; 35.1; 56.5; 113.0; 119.5; 121.9; 123.2; 123.3; 123.5; 125.2 (d, $J_{CP}$=5.4 Hz); 126.3 (d, $J_{CP}$=9.5 Hz); 128.5; 129.9; 132.0 (d, $J_{CP}$=3.0 Hz); 132.6; 136.1; 136.2 (d, $J_{CP}$=6.0 Hz); 143.9 (d, $J_{CP}$=6.7 Hz); 149.3 (d, $J_{CP}$=5.7 Hz); 152.1; 153.8 ppm.

9-(tert-Butyl)-6-((2-isopropyl-5-methylcyclohexyl)oxy)-4-methoxy-2-methyldibenzo[d,f][1,3,2]dioxaphosphepine (6)

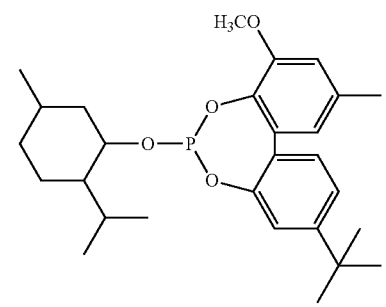

To a stirred suspension of 4'-(tert-butyl)-3-methoxy-5-methyl-[1,1'-biphenyl]-2,2'-diol (0.675 g; 2.36 mmol) in toluene (16 ml) was added triethylamine (2.188 g; 21.62 mmol) and the resulting mixture was added dropwise at 0° C. to a solution of dichloro((−)-menthyloxy)phosphine (0.606 g; 2.36 mmol) in toluene (15 ml). The reaction mixture was stirred overnight and filtered. The filtrate was concentrated to dryness under reduced pressure. Yield: 0.965 g (2.051 mmol; 87%).

Elemental analysis (calc. for $C_{28}H_{39}O_4P$=470.56 g/mol) C, 71.49 (71.46); H, 8.59 (8.35); P, 6.81 (6.58)%.

$^{31}$P-NMR ($CD_2Cl_2$): 153.2; 153.4 ppm.

$^1$H-NMR ($CD_2Cl_2$): (m, 4H); 0.97-1.02 (m, 6H); 1.04-1.39 (m, 3H); 1.41 (m, 9H); 1.46-1.61 (m, 1H); 1.73 (m, 2H); 2.19-2.37 (m, 2H); 2.43 (s, 3H); 3.91 (s, 3H); 4.15-4.28 (m, 1H); 6.87 (m, 2H, $H_{arom}$); 7.20-7.21 (m, 1H, $H_{arom}$); 7.33-7.36 (m, 1H, $H_{arom}$); 7.43-7.45 (m, 1H, $H_{arom}$) ppm.

6-([1,1':3',1''-Terphenyl]-2'-yloxy)-2-isopropyl-8-methoxy-3,10-dimethyldibenzo[d,f][1,3,2]dioxaphosphepine

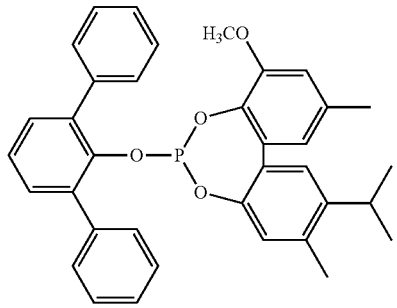

(7)

To a solution of 5'-isopropyl-3-methoxy-4',5-dimethyl-[1,1'-biphenyl]-2,2'-diol (0.478 g; 1.670 mmol) in toluene (12 ml) was added triethylamine (1.548 g; 15.296 mmol). The mixture was cooled to 0° C. and a solution of 2,6-diphenyl-phenoxydichlorophosphine (0.580 g; 1.670 mmol) in toluene (3 ml) was added dropwise. The reaction mixture was stirred overnight and then filtered. The filtrate was concentrated to dryness under reduced pressure, and the resulting solid was dried at 50° C. and purified by column chromatography (dichloromethane, $R_f$=0.8). Yield: 0.642 g (1.144 mmol; 69%).

Elemental analysis (calc. for $C_{36}H_{33}O_4P$=560.63 g/mol) C, 77.07 (77.13); H, 5.73 (5.93); P, 5.56 (5.52)%.

$^{31}$P-NMR (CD$_2$Cl$_2$): 143.7 ppm.

$^{1}$H-NMR (CD$_2$Cl$_2$): (m, 6H); 2.32 (m, 3H); 2.40 (m, 3H); 3.13-3.23 (m, 1H); 3.76 (s, 3H); 6.01 (m, 1H, H$_{arom}$); 6.77 (m, 2H, H$_{arom}$); 7.24 (m, 1H, H$_{arom}$); 7.35-7.39 (m, 1H, H$_{arom}$); 7.41-7.51 (m, 8H, H$_{arom}$); 7.60-7.65 (m, 4H, H$_{arom}$) ppm.

$^{13}$C-NMR (CD$_2$Cl$_2$): 19.3; 21.6; 23.5; 23.6; 29.3; 56.1; 112.7; 121.3; 123.2; 125.0; 126.0; 127.8; 128.6; 129.2; 129.8; 130.7; 131.2; 133.0 (d, $J_{CP}$=3.9 Hz); 134.9; 135.6; 136.5; 136.7; 139.0; 143.8; 146.6 (d, $J_{CP}$=5.4 Hz); 147.4 (d, $J_{CP}$=8.0 Hz); 152.0 (d, $J_{CP}$=2.2 Hz) ppm.

6-(Anthracen-9-yloxy)-2-isopropyl-8-methoxy-3,10-dimethyldibenzo[d,f][1,3,2]dioxaphosphepine

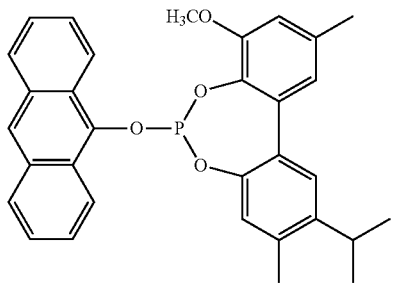

(8)

To a solution of 5'-isopropyl-3-methoxy-4',5-dimethyl-[1,1'-biphenyl]-2,2'-diol (0.359 g; 1.252 mmol) in toluene (7 ml) was added triethylamine (1.161 g; 11.473 mmol), cooled to 0° C. and to this mixture was added dropwise a solution of (anthracen-9-yloxy)dichlorophosphine (0.370 g; 1.252 mmol) in toluene (9 ml). The reaction mixture was stirred overnight and then filtered. The filtrate was concentrated to dryness under reduced pressure. Yield: 0.594 g (1.168 mmol; 93%). Elemental analysis (calc. for $C_{32}H_{29}O_4P$=508.55 g/mol) C, 75.46 (75.58); H, 5.90 (5.75); P, 6.09 (6.09)%.

$^{31}$P-NMR (CD$_2$Cl$_2$): 148.5 ppm.

$^{1}$H-NMR (CD$_2$Cl$_2$): 38 (d, $^2J_{HH}$=6.8 Hz, 3H); 1.39 (d, $^2J_{CP}$=6.8 Hz, 3H); 2.46 (s, 3H); 2.52 (s, 3H); 3.22-3.32 (m, 1H); 3.99 (s, 3H); 6.95 (m, 1H, H$_{arom}$); 7.07 (m, 1H, H$_{arom}$); 7.20 (m, 1H, H$_{arom}$); 7.52 (s, 1H, H$_{arom}$); 7.57-7.68 (m, 4H, H$_{arom}$); 8.10 (m, 2H, H$_{arom}$); 8.39 (m, 1H, H$_{arom}$); 8.79 (m, 2H, H$_{arom}$) ppm.

$^{13}$C-NMR (CD$_2$Cl$_2$): 19.3; 21.7; 23.6; 23.6; 29.5; 56.5; 113.0; 121.9; 123.4; 123.5; 123.8; 125.2; (d, $J_{CP}$=3.3 Hz); 125.7; 126.3 (d, $J_{CP}$=3.3 Hz); 126.7; 128.6 (d, $J_{CP}$=8.7 Hz); 129.4; 132.5 (d, $J_{CP}$=3.6 Hz); 132.6; 136.1; 136.2 (d, $J_{CP}$=6.2 Hz); 137.5; 138.4; 143.9 (d, $J_{CP}$=6.5 Hz); 144.8; 146.9 (d, $J_{CP}$=5.9 Hz); 152.1 ppm.

2-Isopropyl-6-((2-isopropyl-5-methylcyclohexyl)oxy)-8-methoxy-3,10-dimethyldibenzo[d,f][1,3,2]dioxaphosphepine

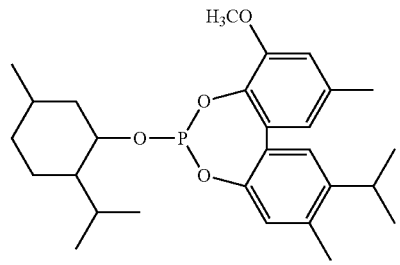

(9)

To a solution of 5'-isopropyl-3-methoxy-4',5-dimethyl-[1,1'-biphenyl]-2,2'-diol (0.664 g; 2.32 mmol) in toluene (16 ml) was added triethylamine (2.152 g; 21.27 mmol) and the resulting mixture added dropwise at 0° C. to a solution of dichloro((−)-menthyloxy)phosphine (0.596 g; 2.32 mmol) in toluene (15 ml). The reaction mixture was stirred overnight and filtered. The filtrate was concentrated to dryness under reduced pressure. Yield: 0.944 g (2.006 mmol; 87%).

Elemental analysis (calc. for $C_{28}H_{39}O_4P$=470.56 g/mol) C, 71.28 (71.46); H, 8.36 (8.35); P, 6.72 (6.58)%.

$^{31}$P-NMR (CD$_2$Cl$_2$): 152.4; 153.7 ppm.

$^{1}$H-NMR (CD$_2$Cl$_2$): (m, 4H); 0.97-1.02 (m, 6H); 1.06-1.29 (m, 2H); 1.32 (m, 6H); 1.35-1.46 (m, 1H); 1.46-1.60 (m, 1H); 1.73 (m, 2H); 2.19-2.37 (m, 2H); 2.40-2.46 (m, 6H); 3.21 (s, 1H); 3.90 (s, 3H); 4.20 (m, 1H); 6.84 (s, 1H, H$_{arom}$); 6.90 (m, 1H, H$_{arom}$); 6.96 (m, 1H, H$_{arom}$); 7.35 (m, 1H, H$_{arom}$) ppm.

6-([1,1':3',1-Terphenyl]-2'-yloxy)-4-methoxy-2,10-dimethyldibenzo[d,f][1,3,2]dioxaphosphepine

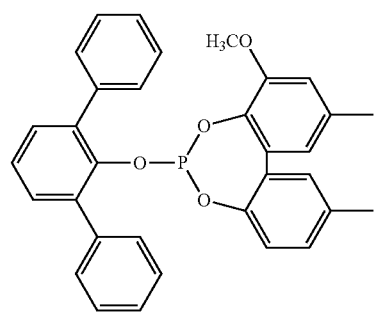

(10)

To a stirred solution of 3-methoxy-5,5'-dimethyl-[1,1'-biphenyl]-2,2'-diol (0.465 g; 1.903 mmol) in toluene (12 ml) was added triethylamine (1.764 g; 17.433 mmol) and the mixture cooled to 0° C. To this mixture was added dropwise a solution of 2,6-diphenylphenoxydichlorophosphine (0.661 g; 1.903 mmol) in toluene (3 ml). The reaction mixture was stirred overnight and then filtered. The filtrate was concentrated to dryness under vacuum and the resulting solid was recrystallized from hexane (20 ml). Yield: 0.804 g (1.550 mmol; 82%).

Elemental analysis (calc. for $C_{33}H_{27}O_4P$=518.55 g/mol) C, 76.38 (76.44); H, 5.18 (5.25); P, 5.97 (5.97)%.

$^{31}$P-NMR (CD$_2$Cl$_2$): 144.9 ppm.

$^1$H-NMR (CD$_2$Cl$_2$): (m, 6H); 3.75 (s, 3H); 5.86 (m, 1H, $H_{arom}$); 6.76 (m, 2H, $H_{arom}$); 6.92 (m, 1H, $H_{arom}$); 7.19 (m, 1H, $H_{arom}$); 7.36 (m, 1H, $H_{arom}$); 7.40-7.55 (m, 8H, $H_{arom}$); 7.60-7.68 (m, 4H, $H_{arom}$) ppm.

$^{13}$C-NMR (CD$_2$Cl$_2$): 20.9; 21.6; 56.0; 112.9; 121.4; 121.8; 125.1; 127.7; 128.8; 129.9; 130.1; 130.7; 131.3; 132.7 (d, $J_{CP}$=3.5 Hz); 134.4; 135.1; 135.7; 136.4 (d, $J_{CP}$=4.4 Hz); 139.0; 146.4 (d, $J_{CP}$=6.8 Hz); 147.6 (d, $J_{CP}$=7.4 Hz); 152.0 (d, $J_{CP}$=2.5 Hz) ppm.

6-(Anthracen-9-yloxy)-4-methoxy-2,10-dimethyl-dibenzo[d,f][1,3,2]dioxaphosphepine

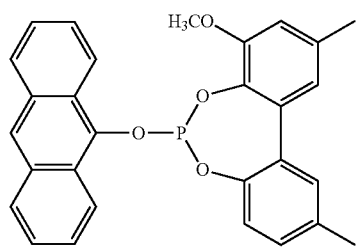

(11)

To a stirred solution of 3-methoxy-5,5'-dimethyl-[1,1'-biphenyl]-2,2'-diol (0.655 g; 2.68 mmol) in toluene (16 ml) was added triethylamine (2.487 g; 24.58 mmol) and the mixture cooled to 0° C. To this mixture was added dropwise a solution of (anthracen-9-yloxy)dichlorophosphine (0.792 g; 2.683 mmol) in toluene (18 ml). The reaction mixture was stirred overnight and then filtered. The filtrate was concentrated to dryness under vacuum and the residue dried at 50° C./0.1 mbar for 3 h. Yield: 1.020 g (2.187 mmol; 82%).

Elemental analysis (calc. for $C_{29}H_{23}O_4P$=466.47 g/mol) C, 74.58 (74.67); H, 5.19 (4.97); P, 6.78 (6.64)%.

$^{31}$P-NMR (CD$_2$Cl$_2$): 148.6 ppm.

$^1$H-NMR (CD$_2$Cl$_2$): 2.51 (m, 6H); 3.99 (s, 3H); 6.96 (m, 1H, $H_{arom}$); 7.06 (m, 1H, $H_{arom}$); 7.32-7.37 (m, 2H, $H_{arom}$); 7.48 (m, 1H, $H_{arom}$); 7.57-7.69 (m, 4H, $H_{arom}$); 8.10 (m, 2H, $H_{arom}$); 8.39 (m, 1H, $H_{arom}$); 8.79 (m, 2H, $H_{arom}$) ppm.

$^{13}$C-NMR (CD$_2$Cl$_2$): 21.1; 21.7; 56.4; 113.2; 122.0; 122.2; 123.3; 123.5; 125.1 (d, $J_{CP}$=3.7 Hz); 126.2; 126.3; 128.5; 130.3; 130.9; 131.3 (d, $J_{CP}$=3.2 Hz); 132.1 (d, $J_{CP}$=3.3 Hz); 132.5 (d, $J_{CP}$=2.0 Hz); 135.7; 136.1; 136.3 (d, $J_{CP}$=5.8 Hz); 143.9 (d, $J_{CP}$=7.1 Hz); 147.3 (d, $J_{CP}$=5.4 Hz); 152.0 (d, $J_{CP}$=2.0 Hz) ppm.

6-((2-Isopropyl-5-methylcyclohexyl)oxy)-4-methoxy-2,10-dimethyldibenzo[d,f][1,3,2]dioxaphosphepine

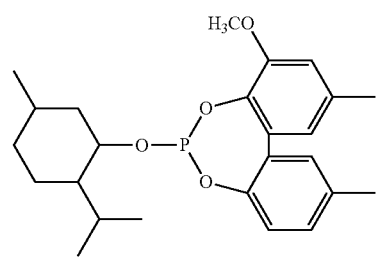

(12)

To a stirred suspension of 3-methoxy-5,5'-dimethyl-[1,1'-biphenyl]-2,2'-diol (0.56 g; 2.3 mmol) in toluene (16 ml) was added triethylamine (2.132 g; 21.07 mmol) and the resulting mixture added dropwise at 0° C. to a solution of dichloro((−)-menthyloxy)phosphine (0.591 g; 2.3 mmol) in toluene (15 ml). The reaction mixture was stirred overnight and filtered. The filtrate was concentrated to dryness under reduced pressure. Yield: 0.860 g (2.01 mmol; 87%).

Elemental analysis (calc. for $C_{25}H_{33}O_4P$=428.48 g/mol) C, 70.26 (70.07); H, 7.71 (7.76); P, 7.09 (7.23)%.

$^{31}$P-NMR (CD$_2$Cl$_2$): 152.9; 153.8 ppm.

$^1$H-NMR (CD$_2$Cl$_2$): (m, 4H); 0.96-1.01 (m, 6H); 1.04-1.46 (m, 3H); 1.46-1.59 (m, 1H); 1.72 (m, 2H); 2.17-2.37 (m, 2H); 2.43 (m, 6H); 3.90 (s, 3H); 4.20 (m, 1H); 6.85 (m, 1H, $H_{arom}$); 6.90 (m, 1H, $H_{arom}$); 7.06 (m, 1H, $H_{arom}$); 7.20 (m, 1H, $H_{arom}$); 7.31 (m, 1H, $H_{arom}$) ppm.

6-([1,1':3',1''-Terphenyl]-2'-yloxy)-4-methoxy-2,8,10-trimethyldibenzo[d,f][1,3,2]dioxaphosphepine

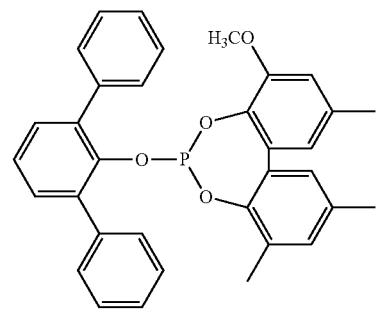

(13)

To a solution of 3-methoxy-3',5,5'-trimethyl-[1,1'-biphenyl]-2,2'-diol (0.492 g; 1.903 mmol) in toluene (18 ml) was added triethylamine (1.764 g; 17.435 mmol) and the mixture cooled to 0° C. To this mixture was added dropwise a solution of 2,6-diphenylphenoxydichlorophosphine (0.727 g; 2.094 mmol) in toluene (3 ml). The reaction mixture was stirred overnight and then filtered. The filtrate was concentrated to dryness under reduced pressure, and the resulting solid was dried at 50° C./0.1 mbar and purified by column chromatography (hexane/dichloromethane, 1:1, $R_f$=0.5). Yield: 0.946 g (1.776 mmol; 81%).

Elemental analysis (calc. for $C_{34}H_{29}O_4P$=532.57 g/mol) C, 76.56 (76.68); H, 5.44 (5.49); P, 5.95 (5.82)%.

$^{31}$P-NMR (CD$_2$Cl$_2$): 145.6 ppm.

$^1$H-NMR (CD$_2$Cl$_2$): (m, 3H); 2.42 (m, 6H); 3.84 (s, 3H); 6.77 (m, 2H, H$_{arom}$); 7.03 (m, 2H, H$_{arom}$); 7.29-7.34 (m, 5H, H$_{arom}$); 7.34-7.37 (m, 1H, H$_{arom}$); 7.37-7.40 (m, 1H, H$_{arom}$); 7.44 (m, 1H, H$_{arom}$); 7.47 (m, 1H, H$_{arom}$); 7.55-7.62 (m, 4H, H$_{arom}$) ppm.

$^{13}$C-NMR (CD$_2$Cl$_2$): 17.0; 21.0; 21.6; 56.3; 112.8; 122.0; 125.0; 127.4; 128.2; 128.3; 129.3; 129.8; 130.3; 130.5; 130.8 (d, J$_{CP}$=3.3 Hz); 131.0; 131.4; 132.7 (d, J$_{CP}$=3.6 Hz); 134.2; 135.1; 136.0 (d, J$_{CP}$=3.1 Hz); 138.9; 139.0; 146.2; 146.3 (d, J$_{CP}$=6.9 Hz); 151.7 (d, J$_{CP}$=2.0 Hz) ppm.

6-(Anthracen-9-yloxy)-4-methoxy-2,8,10-trimethyl-dibenzo[d,f][1,3,2]dioxaphosphepine

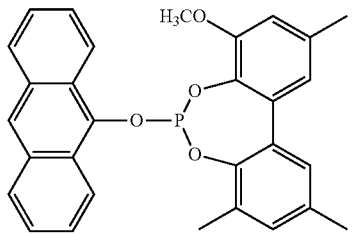

(14)

To a solution of 3-methoxy-3',5,5'-trimethyl-[1,1'-biphenyl]-2,2'-diol (0.409 g; 1.58 mmol) in toluene (9 ml) was added triethylamine (2.468 g; 14.51 mmol), cooled to 0° C. and to this mixture was added dropwise a solution of (anthracen-9-yloxy)dichlorophosphine (0.467 g; 1.584 mmol) in toluene (11 ml). The reaction mixture was stirred overnight and then filtered. The filtrate was concentrated to dryness under vacuum and the resulting residue recrystallized from hexane (17 ml). Yield: 0.511 g (1.063 mmol; 67%).

Elemental analysis (calc. for C$_{30}$H$_{25}$O$_4$P=480.50 g/mol) C, 74.53 (74.99); H, 5.53 (5.24); P, 6.48 (6.45)%.

$^{31}$P-NMR (CD$_2$Cl$_2$): 147.7 ppm.

$^1$H-NMR (CD$_2$Cl$_2$): 2.46-2.50 (m, 9H); 4.02 (s, 3H); 6.96 (m, 1H, H$_{arom}$); 7.05 (m, 1H, H$_{arom}$); 7.20 (m, 1H, H$_{arom}$); 7.30 (m, 1H, H$_{arom}$); 7.56-7.68 (m, 4H, H$_{arom}$); 8.10 (m, 2H, H$_{arom}$); 8.40 (m, 1H, H$_{arom}$); 8.88 (m, 2H, H$_{arom}$) ppm.

$^{13}$C-NMR (CD$_2$Cl$_2$): 17.0; 21.1; 21.7; 56.3; 113.0; 122.2; 123.4; 123.5; 125.3 (d, J$_{CP}$=3.6 Hz); 125.7; 126.3 (d, J$_{CP}$=5.5 Hz); 128.4; 128.5; 130.9; 131.6 (d, J$_{CP}$=3.7 Hz); 132.0; 132.0; 132.5; 135.4; 135.8; 136.8 (d, J$_{CP}$=8.0 Hz); 143.9 (d, J$_{CP}$=7.4 Hz); 145.3 (d, J$_{CP}$=4.0 Hz); 151.9 ppm.

6-((2-Isopropyl-5-methylcyclohexyl)oxy)-4-methoxy-2,8,10-trimethyldibenzo[d,f][1,3,2]dioxaphosphepine

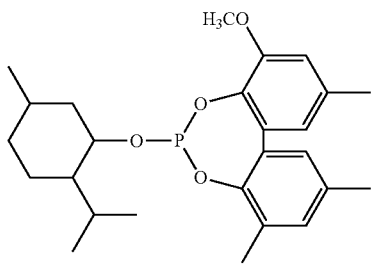

(15)

To a solution of 3-methoxy-3',5,5'-trimethyl-[1,1'-biphenyl]-2,2'-diol (0.594 g; 2.3 mmol) in toluene (16 ml) was added triethylamine (2.132 g; 21.07 mmol), and the mixture was added dropwise at 0° C. to a solution of dichloro((−)-menthyloxy)phosphine (0.591 g; 2.3 mmol) in toluene (15 ml). The reaction mixture was stirred overnight and filtered. The filtrate was concentrated to dryness under reduced pressure. Dissolution of the residue in dichloromethane (1.5 ml) was followed immediately by crystallization. The resulting solid was dried at room temperature under reduced pressure. Yield: 0.337 g (0.76 mmol; 33%). Elemental analysis (calc. for C$_{26}$H$_{35}$O$_4$P=442.51 g/mol): C, 70.33 (70.57); H, 8.05 (7.97); P 7.22 (7.00) %.

$^{31}$P-NMR (CD$_2$Cl$_2$): 105.4; 153.6 ppm.

$^1$H-NMR (CD$_2$Cl$_2$): 0.86-0.93 (m, 4H); 0.95-1.01 (m, 6H); 1.03-1.19 (m, 1H); 1.19-1.34 (m, 1H); 1.34-1.46 (m, 1H); 1.46-1.61 (m, 1H); 1.67-1.77 (m, 2H); 2.12-2.35 (m, 2H); 2.35-2.44 (m, 9H); 3.89 (s, 3H); 4.20 (m, 1H); 6.86 (m, 2H, H$_{arom}$); 7.11 (m, 2H, H$_{arom}$) ppm.

6-([1,1':3',1''-Terphenyl]-2'-yloxy)-8-methoxy-2,3,10-trimethyldibenzo[d,f][1,3,2]dioxaphosphepine

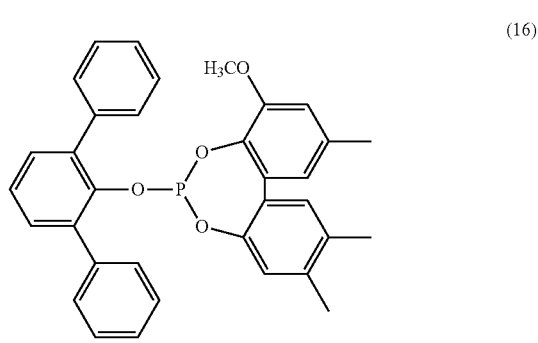 [SMILES: COc1cc(C)cc2c1op(Oc1c(-c3ccccc3)cccc1-c1ccccc1)oc1cc(C)c(C)cc12]

(16)

To a stirred suspension of 3-methoxy-4',5,5'-trimethyl-[1,1'-biphenyl]-2,2'-diol (0.492 g; 1.903 mmol) in toluene (18 ml) was added triethylamine (1.764 g; 17.435 mmol) and the mixture cooled to 0° C. To this mixture was added dropwise a solution of 2,6-diphenylphenoxydichlorophosphine (0.727 g; 2.094 mmol) in toluene (3 ml). The reaction mixture was stirred overnight and then filtered. The filtrate was concentrated to dryness under reduced pressure, and the resulting solid was dried at 50° C./0.1 mbar and purified by column chromatography (hexane/dichloromethane, 1:2, R$_f$=0.3). Alternatively, the substance was recrystallized from hexane (23 ml). Yield: 0.749 g (1.406 mmol; 74%).

Elemental analysis (calc. for C$_{34}$H$_{29}$O$_4$P=532.57 g/mol) C, 76.56 (76.68); H, 5.31 (5.49); P, 5.90 (5.82)%.

$^{31}$P-NMR (CD$_2$Cl$_2$): 144.0 ppm.

$^1$H-NMR (CD$_2$Cl$_2$): (m, 3H); 2.33 (m, 3H); 2.41 (m, 3H); 3.77 (s, 3H); 6.02 (m, 1H, H$_{arom}$); 6.78 (m, 2H, H$_{arom}$); 7.18 (m, 1H, H$_{arom}$); 7.35-7.41 (m, 1H, H$_{arom}$); 7.42-7.55 (m, 8H, H$_{arom}$); 7.64-7.70 (m, 4H, H$_{arom}$) ppm.

$^{13}$C-NMR (CD$_2$Cl$_2$): 19.3; 19.9; 21.6; 56.1; 112.7; 121.4; 122.8; 125.1; 127.5 (d, J$_{CP}$=2.7 Hz); 127.8; 128.6; 130.4; 130.5; 130.7; 131.3; 132.8 (d, J$_{CP}$=3.8 Hz); 133.4; 135.1; 135.6; 136.6 (d, J$_{CP}$=4.2 Hz); 138.1; 139.0; 146.6 (d, J$_{CP}$=5.7 Hz); 147.8 (d, J$_{CP}$=8.1 Hz); 152.0 (d, J$_{CP}$=2.0 Hz) ppm.

6-(Anthracen-9-yloxy)-8-methoxy-2,3,10-trimethyl-dibenzo[d,f][1,3,2]dioxaphosphepine

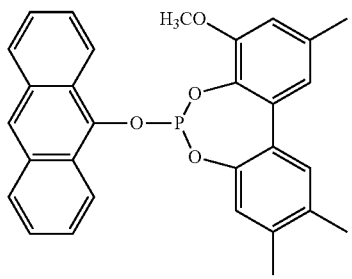

(17)

To a solution of 3-methoxy-4',5,5'-trimethyl-[1,1'-biphenyl]-2,2'-diol (0.518 g; 2.00 mmol) in toluene (11 ml) was added triethylamine (1.857 g; 18.35 mmol) and the mixture cooled to 0° C. To this mixture was added dropwise a solution of (anthracen-9-yloxy)dichlorophosphine (0.591 g; 2.00 mmol) in toluene (8 ml). After addition of further toluene (30 ml), the reaction mixture was stirred overnight. The mixture was then filtered and the solvent was removed under reduced pressure. The residue obtained was taken up in toluene (11 ml) and the resulting suspension gently heated and then filtered. The filtrate was concentrated to dryness under vacuum and the residue obtained dried at 50° C./0.1 mbar. Yield: 0.489 g (1.018 mmol; 51%). Elemental analysis (calc. for $C_{30}H_{25}O_4P$=480.50 g/mol) C, 74.77 (74.99); H, 5.10 (5.24); P, 6.47 (6.45)%.

$^{31}$P-NMR (CD$_2$Cl$_2$): 148.2 ppm.

$^1$H-NMR (CD$_2$Cl$_2$): 2.38 (m, 6H); 2.49 (m, 3H); 3.98 (s, 3H); 6.93 (m, 1H, H$_{arom}$); 7.03 (m, 1H, H$_{arom}$); 7.19 (m, 1H, H$_{arom}$); 7.40 (m, 1H, H$_{arom}$); 7.56-7.68 (m, 4H, H$_{arom}$); 8.09 (m, 2H, H$_{arom}$); 8.38 (m, 1H, H$_{arom}$); 8.76 (m, 2H, H$_{arom}$) ppm.

$^{13}$C-NMR (CD$_2$Cl$_2$): 19.4; 19.8; 21.7; 56.4; 112.9; 121.8; 123.3; 123.3; 123.4; 125.1 (d, $J_{CP}$=3.5 Hz); 125.6 (d, $J_{CP}$=3.5 Hz); 126.1; 126.2; 128.4; 131.1; 132.1 (d, $J_{CP}$=3.1 Hz); 132.5; 134.4; 136.0; 136.2 (d, $J_{CP}$=6.0 Hz); 138.8; 143.9 (d, $J_{CP}$=6.9 Hz); 147.2 (d, $J_{CP}$=5.7 Hz); 152.0 ppm.

6-((2-Isopropyl-5-methylcyclohexyl)oxy)-8-methoxy-2,3,10-trimethyldibenzo[d,f][1,3,2]dioxaphosphepine

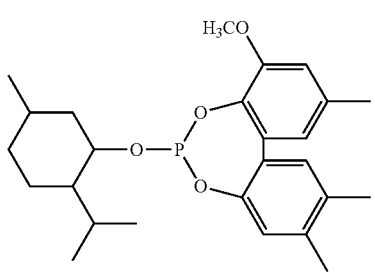

(18)

To a stirred solution of 3-methoxy-4',5,5'-trimethyl-[1,1'-biphenyl]-2,2'-diol (0.592 g; 2.30 mmol) in toluene (16 ml) was added triethylamine (2.127 g; 21.02 mmol) and the resulting mixture added dropwise at 0° C. to a solution of dichloro((−)-menthyloxy)phosphine (0.588 g; 2.30 mmol) in toluene (15 ml). The reaction mixture was stirred overnight and then filtered. The filtrate was concentrated to dryness under reduced pressure. Yield: 0.679 g (1.535 mmol; 67%).

Elemental analysis (calc. for $C_{26}H_{35}O_4P$=442.51 g/mol) C, 70.70 (70.57); H, 8.32 (7.97) %. $^{31}$P-NMR (CD$_2$Cl$_2$): 152.5; 153.5 ppm.

$^1$H-NMR (CD$_2$Cl$_2$): 0.90 (m, 4H); 0.96-1.02 (m, 6H); 1.05-1.45 (m, 3H); 1.46-1.59 (m, 1H); 1.73 (m, 2H); 2.17-2.32 (m, 2H); 2.34 (m, 6H); 2.43 (m, 3H); 3.90 (s, 3H); 4.13-4.25 (m, 1H); 6.83 (s, 1H, H$_{arom}$); 6.89 (m, 1H, H$_{arom}$); 6.97 (m, 1H, H$_{arom}$); 7.26 (m, 1H, H$_{arom}$) ppm.

6-(Anthracen-9-yloxy)-4-(tert-butyl)-2-methoxy-benzo[d]naphtho[1,2-f][1,3,2]dioxaphosphepine

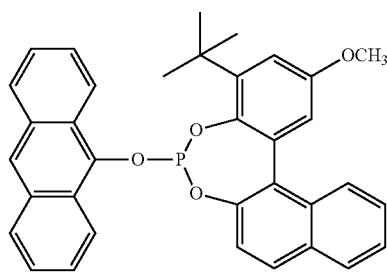

(19)

To a solution of 1-(3-(tert-butyl)-2-hydroxy-5-methoxyphenyl)naphthalen-2-ol (0.730 g; 2.26 mmol) in toluene (14 ml) was added triethylamine (2.097 g; 20.73 mmol) and to this mixture at 0° C. was added dropwise a solution of (anthracen-9-yloxy)dichlorophosphine (0.668 g; 2.26 mmol) in toluene (10 ml). The reaction mixture was stirred overnight and then filtered. The filtrate was concentrated to dryness under vacuum and the resulting residue recrystallized from hexane (28 ml). Yield: 0.708 g (1.30 mmol; 58%). Elemental analysis (calc. for $C_{35}H_{29}O_4P$=544.58 g/mol) C, 76.96 (77.19); H, 5.38 (5.37); P, 5.66 (5.69)%.

$^{31}$P-NMR (CD$_2$Cl$_2$): 150.0 ppm.

$^1$H-NMR (CD$_2$Cl$_2$): 53 (s, 9H); 3.88 (s, 3H); 7.10 (d, $J_{HH}$=3.1 Hz, 1H, H$_{arom}$); 7.18 (d, $J_{HH}$=3.1 Hz, 1H, H$_{arom}$); 7.54-7.64 (m, 6H, H$_{arom}$); 7.78 (m, 1H, H$_{arom}$); 7.99-8.10 (m, 4H, H$_{arom}$); 8.18-8.22 (m, 1H, H$_{arom}$); 8.38 (m, 1H, H$_{arom}$); 8.62 (m, 2H, H$_{arom}$) ppm.

$^{13}$C-NMR (CD$_2$Cl$_2$): 31.2; 35.8; 56.1; 115.0; 115.1; 121.7; 123.1; 123.7; 125.0 (d, $J_{CP}$=3.7 Hz); 125.7; 126.0; 126.2; 126.4; 127.3; 128.6; 128.9; 129.4; 130.1; 130.7 (d, $J_{CP}$=5.0 Hz); 132.4; 132.5; 133.0; 138.4; 142.1; 143.7 (d, $J_{CP}$=7.2 Hz); 144.4; 146.8 (d, $J_{CP}$=5.5 Hz); 156.1 ppm.

6-([1,1':3',1''-Terphenyl]-2'-yloxy)dibenzo[d,f][1,3,2]dioxaphosphepine

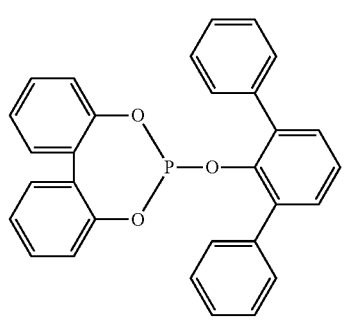

(A)

To a solution of 2,6-diphenylphenol (0.491 g; 1.99 mmol) in toluene (9 ml) was added triethylamine (1.851 g; 18.293 mmol) and the resulting mixture added dropwise at 0° C. to a solution of 6-chlorodibenzo[d,f][1,3,2]dioxaphosphepine (0.500 g; 1.99 mmol) in toluene (9 ml). The reaction mixture was stirred overnight and then filtered. The filtrate was concentrated to dryness under vacuum and the resulting residue recrystallized from hot toluene (3 ml). Yield: 0.536 g (1.164 mmol; 58%).

Elemental analysis (calc. for $C_{30}H_{21}O_3P$=460.44 g/mol) C, 78.30 (78.25); H, 4.72 (4.60) %. $^{31}$P-NMR ($CD_2Cl_2$): 146.0 ppm.

$^1$H-NMR ($CD_2Cl_2$): 6.12 (m, 2H); 7.21 (m, 4H); 7.35-7.40 (m, 3H); 7.43-7.46 (m, 2H); 7.52-7.57 (m, 6H); 7.59-7.64 (m, 4H) ppm.

$^{13}$C-NMR ($CD_2Cl_2$): 122.5; 125.2; 125.5; 127.9; 128.9; 129.5; 129.8; 131.1; 131.2; 136.4; 136.5; 138.9; 146.5 (d, $J_{CP}$=8.5 Hz); 149.0 (d, $J_{CP}$=4.7 Hz) ppm.

6-([1,1':3',1''-Terphenyl]-2'-yloxy)-4,8-di-tert-butyl-2,10-dimethoxydibenzo-[d,f][1,3,2]dioxaphosphepine

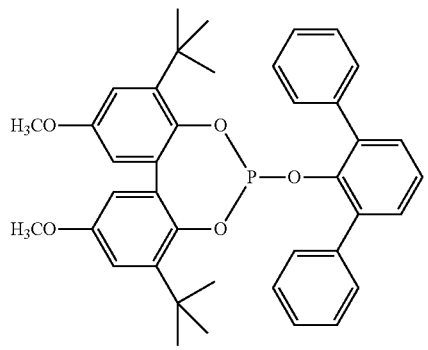

(B)

To a solution of 2,6-diphenylphenol (0.411 g; 1.65 mmol) in toluene (8 ml) was added triethylamine (1.529 g; 15.11 mmol) and the resulting mixture added dropwise at 0° C. to a solution of 4,8-di-tert-butyl-6-chloro-2,10-dimethoxy-dibenzo[d,f][1,3,2]dioxaphosphepine (0.697 g; 1.65 mmol) in toluene (6 ml). The reaction mixture was stirred at room temperature overnight and at 70° C. for 5 h. The mixture was then filtered and the filtrate was concentrated to dryness under vacuum. The residue obtained was recrystallized from hexane (4 ml). Yield: 0.417 g (0.659 mmol; 40%).

Elemental analysis (calc. for $C_{40}H_{41}O_5P$=632.70 g/mol) C, 75.95 (75.93); H, 6.52 (6.53); P, 5.01 (5.00)%.

$^{31}$P-NMR ($CD_2Cl_2$): 140.9 ppm.

$^1$H-NMR ($CD_2Cl_2$): 1.37 (s, 18H); 3.84 (s, 6H); 6.51 (d, $^5J_{HH}$=3.1 Hz, 2H, $H_{arom}$); 6.89-7.95 (m, br, 15H, $H_{arom}$) ppm.

$^{13}$C NMR ($CD_2Cl_2$): 31.1; 35.5; 55.9; 113.0; 114.5; 125.2; 126.5-131.0 (broad, overlapping signals); 133.8 (d, $J_{CP}$=4.0 Hz); 141.5 (d, $J_{CP}$=6.3 Hz); 142.6; 144.8; 156.1 ppm.

6-(Anthracen-9-yloxy)-2,4,8,10-tetra-tert-butyldibenzo[d,f][1,3,2]dioxaphosphepine

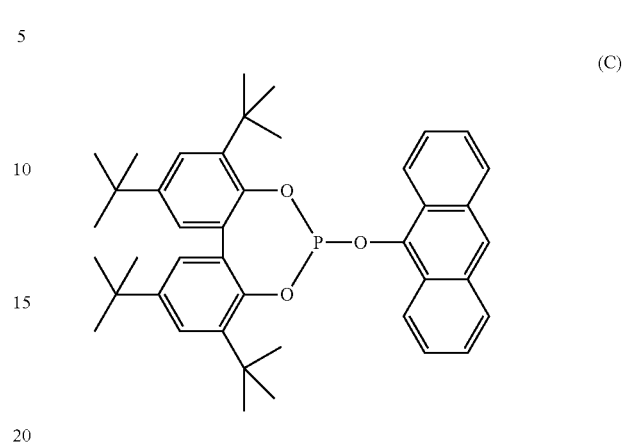

(C)

To a stirred suspension of anthracen-9-ol (0.281 g; 1.45 mmol) in toluene (7 ml) was added triethylamine (1.344 g; 13.28 mmol) and the resulting mixture added dropwise at 0° C. to a solution of 2,4,8,10-tetra-tert-butyl-6-chlorodibenzo [d,f][1,3,2]dioxaphosphepine (0.724 g; 1.52 mmol) in toluene (6 ml). The reaction mixture was stirred overnight and filtered. The filtrate was concentrated to dryness under vacuum and the resulting residue recrystallized from hexane (4 ml). Yield: 0.559 g (0.883 mmol; 61%).

Elemental analysis (calc. for $C_{42}H_{49}O_3P$=632.78 g/mol) C, 79.83 (79.71); H, 7.61 (7.81); P, 5.01 (4.89)%.

$^{31}$P-NMR ($CD_2Cl_2$): 140.7 ppm.

$^1$H-NMR ($CD_2Cl_2$): 1.41 (s, 18H, $C(CH_3)_3$); 1.50 (s, 18H, $C(CH_3)_3$); 7.40 (d, $^5J_{HH}$=2.4 Hz, 2H, $H_{arom}$); 7.43-7.56 (m, 4H, $H_{arom}$); 7.60 (d, $^5J_{HH}$=2.4 Hz, 2H, $H_{arom}$); 8.05 (m, 2H, $H_{arom}$); 8.34 (s, 1H, $H_{arom}$); 8.38 (m, 2H, $H_{arom}$) ppm.

$^{13}$C-NMR ($CD_2Cl_2$): 31.2; 31.2; 31.8; 35.1; 35.7; 123.1; 123.7 (d, $J_{CP}$=5.3 Hz); 124.8; 125.0; 125.8; 126.0; 127.2; 128.4; 132.6; 133.3 (d, $J_{CP}$=3.7 Hz); 141.0; 143.5; 145.8 (d, $J_{CP}$=6.2 Hz); 147.7 ppm.

Procedure for the Catalysis Experiments

The hydroformylation was conducted in a 200 ml autoclave equipped with pressure-retaining valve, gas flow meter, sparging stirrer and pressure pipette from Premex Reactor AG, Lengau, Switzerland. To minimize the influence of moisture and oxygen, the toluene used as solvent was dried with sodium ketyl and distilled under argon. The following substrates used as substrate were heated at reflux over sodium and distilled under argon for several hours: 1-octene (Aldrich), cis/trans-2-pentene (Aldrich) and n-octenes (Oxeno GmbH, octene isomer mixture of 1-octene: 3.3%; cis+trans-2-octene; 48.5%; cis+trans-3-octene: 29.2%; cis+trans-octene-4: 16.4%; structurally isomeric octenes: 2.6%).

For the experiments, the following solutions of rhodium in the form of [(acac)Rh(COD)](acac=acetylacetonate anion; COD=1,5-cyclooctadiene, Umicore) as the catalyst precursor in toluene were introduced into the autoclave under an argon atmosphere: for experiments at 100 ppm by mass of rhodium 10 ml of a 4.31 millimolar solution, for 40 or 60 ppm by mass the same amount of an appropriately diluted solution. The appropriate amount of the phosphite compound (5 ligand equivalents per unit rhodium) dissolved in toluene was then added. By addition of further toluene (the total amount of toluene was determined for the GC analysis, see below), the initial volume of the catalyst solution was adjusted to 41.0 ml. The mass of toluene introduced was determined in each case. Weight of n-octenes: 10.70 g (95.35 mmol). The autoclave was heated while stirring (1500 rpm) to the temperatures stated in each case at a total gas pressure (synthesis gas: Linde; $H_2$ (99.999%):CO (99.997%)=1:1) of a) 42 bar for a final pressure of 50 bar or b) 12 bar for the final pressure of 20 bar. After reaching the reaction temperature, the synthesis gas pressure was increased to a) 48.5 bar for a final pressure of 50 bar or b) 19.5 bar for a final pressure of 20 bar and the reactant was introduced under a positive pressure of about 3 bar set in the pressure pipette. The reaction was conducted at a constant pressure of 50 or 20 bar in each case (closed-loop pressure controller from Bronkhorst, the Netherlands) over 4 h. Simultaneously with the reaction, at time intervals of 3 sec., the current gas flow was determined (flow meter from Bronkhorst). After the reaction time had elapsed, the autoclave was cooled to room temperature, decompressed while stirring and purged with argon. 1 ml of each reaction mixture was removed immediately after the stirrer had been switched off, diluted with 5 ml of pentane and analysed by gas chromatography: HP 5890 Series II plus, PONA, 50 m×0.2 mm×0.5 μm; residual olefin and aldehyde were determined quantitatively against the toluene solvent as internal standard.

Table 1 lists the results of the catalysis experiments.

The inventive compounds are identified here by *.

Comparative ligands used were the ligands A, B and C.
Solvent: toluene
Yld.=yield
p=pressure in [bar]
T=temperature in [° C.]
t=time in [h]
[Rh]=rhodium concentration in [ppm]
L/Rh=ratio of ligand to rhodium

TABLE 1

| | | | n-Octenes | | | |
|---|---|---|---|---|---|---|
| Ligand | p (bar) | T (° C.) | t (h) | [Rh] (ppm) | L/Rh | Sol. | Yld. (%) |
| 1* | 20 | 120 | 4 | 100 | 5 | Tol | 96 |
| 1* | 50 | 120 | 4 | 100 | 5 | Tol | 96 |
| 2* | 50 | 120 | 4 | 100 | 5 | Tol | 92 |
| 2* | 20 | 120 | 4 | 100 | 5 | Tol | 91 |
| 3* | 50 | 120 | 4 | 100 | 5 | Tol | 96 |
| 4* | 20 | 120 | 4 | 100 | 5 | Tol | 88 |
| 5* | 50 | 120 | 4 | 100 | 5 | Tol | 100 |
| 6* | 20 | 120 | 4 | 100 | 5 | Tol | 92 |
| 7* | 20 | 120 | 4 | 100 | 5 | Tol | 95 |
| 8* | 50 | 120 | 4 | 100 | 5 | Tol | 99 |
| 9* | 50 | 120 | 4 | 100 | 5 | Tol | 95 |
| 9* | 20 | 120 | 4 | 100 | 5 | Tol | 91 |
| 10* | 20 | 120 | 4 | 100 | 5 | Tol | 93 |
| 10* | 50 | 120 | 4 | 100 | 5 | Tol | 95 |
| 11* | 50 | 120 | 4 | 100 | 5 | Tol | 99 |
| 11* | 20 | 120 | 4 | 100 | 5 | Tol | 98 |
| 11* | 50 | 120 | 4 | 40 | 5 | Tol | 100 |
| 11* | 50 | 120 | 4 | 60 | 5 | Tol | 100 |
| 12* | 50 | 120 | 4 | 100 | 5 | Tol | 92 |
| 13* | 20 | 120 | 4 | 100 | 5 | Tol | 91 |
| 14* | 50 | 120 | 4 | 100 | 5 | Tol | 99 |
| 14* | 20 | 120 | 4 | 100 | 5 | Tol | 98 |
| 14* | 50 | 120 | 4 | 40 | 5 | Tol | 99 |
| 14* | 50 | 120 | 4 | 60 | 5 | Tol | 100 |
| 15* | 50 | 120 | 4 | 100 | 5 | Tol | 99 |
| 16* | 20 | 120 | 4 | 100 | 5 | Tol | 97 |
| 17* | 50 | 120 | 4 | 100 | 5 | Tol | 99 |
| 18* | 50 | 120 | 4 | 100 | 5 | Tol | 96 |
| 19* | 50 | 120 | 4 | 100 | 5 | Tol | 98 |
| A | 50 | 120 | 4 | 100 | 5 | Tol | 91 |

TABLE 1-continued

| | | | n-Octenes | | | |
|---|---|---|---|---|---|---|
| Ligand | p (bar) | T (° C.) | t (h) | [Rh] (ppm) | L/Rh | Sol. | Yld. (%) |
| B | 20 | 120 | 4 | 100 | 5 | Tol | 29 |
| C | 20 | 120 | 4 | 100 | 5 | Tol | 86 |

As can be inferred from Table 1, the inventive compounds are notable for very good yields in the hydroformylation of olefin mixtures, specifically the n-octenes, containing both internal and terminal olefins. All the inventive compounds have a yield which is better than that achievable with the comparative ligands A (50 bar), B (20 bar) and C (20 bar) at the corresponding pressures. Thus, the yield at a pressure of 50 bar was always above the value of 91% which was achieved with the comparative ligand A.

Especially at a pressure of 20 bar, the inventive compounds are notable for much better yields than the comparative ligands B and C.

As the experimental results show, the stated object is achieved by the inventive compounds.

It has thus been possible for the first time to generate monophosphites which contain an unsymmetric biaryl unit and have very good hydroformylation properties. This was demonstrated by a multitude of examples. Such specific structures and ligands of this kind were entirely unknown and unobtainable to date.

These monophosphites have a novel kind of asymmetry. The special feature here is the asymmetry within the biaryl unit, which leads to unsymmetric monophosphites. These unsymmetric monophosphites are thus entirely different in structural terms from the unsymmetric monophosphites described in the related art, in which the asymmetry is caused by the radical (X) bonded to the third oxygen.

European patent application EP14196197.9 filed Dec. 4, 2014, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A monophosphite compound of structure (I) or structure (II):

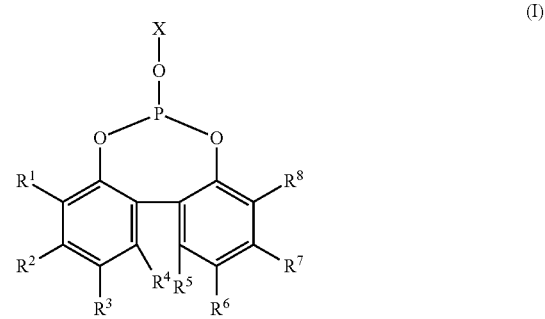

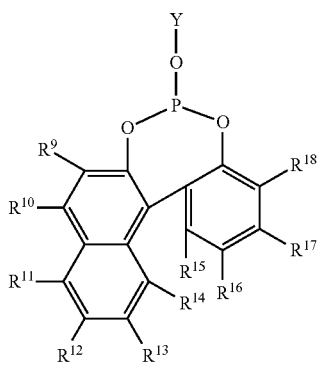

(II)

wherein $R^1$, $R^2$, $R^3$, $R^4$, $R^5$, $R^6$, $R^7$, $R^8$ are each independently —H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —$SO_3H$, —CN, —$NH_2$ or —N[($C_1$-$C_{12}$)-alkyl]$_2$;

$R^9$, $R^{10}$, $R^{11}$, $R^{12}$, $R^{13}$, $R^{14}$, $R^{15}$, $R^{16}$, $R^{17}$, $R^{18}$ are each independently-H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —$SO_3H$, —$NH_2$ or —N[($C_1$-$C_{12}$)-alkyl]$_2$;

X and Y are each —($C_1$-$C_{12}$)-alkyl, —($C_6$-$C_{20}$)-aryl, —($C_3$-$C_{12}$)-cycloalkyl, or —($C_3$-$C_{12}$)-heterocycloalkyl, wherein the two R radicals in at least one of the four following radical pairs are not the same: $R^1$ and $R^8$, $R^2$ and $R^7$, $R^3$ and $R^6$, $R^4$ and $R^5$;

and the $R^3$ and $R^4$ radicals are not joined to one another via a carbon chain;

wherein when any of $R^1$ to $R^{18}$ comprises any of an alkyl and an aryl group, the alkyl group and the aryl group may optionally be substituted.

2. The monophosphite compound according to claim 1, wherein $R^1$, $R^2$, $R^3$, $R^4$, $R^5$, $R^6$, $R^7$, $R^8$ are each independently —H, —($C_1$-$C_{12}$)-alkyl, —O—($C_1$-$C_{12}$)-alkyl, —O—($C_6$-$C_{20}$)-aryl, —S-alkyl or —S-aryl.

3. The monophosphite compound according to claim 1, wherein $R^9$, $R^{10}$, $R^{11}$, $R^{12}$, $R^{13}$, $R^{14}$, $R^{15}$, $R^{16}$, $R^{17}$, $R^{18}$ are each independently —H, —($C_1$-$C_{12}$)-alkyl, —O—($C_1$-$C_{12}$)-alkyl, —O—($C_6$-$C_{20}$)-aryl, —S-alkyl or —S-aryl.

4. The monophosphite compound according to claim 1, wherein X is —($C_1$-$C_{12}$)-alkyl, —($C_6$-$C_{20}$)-aryl or —($C_3$-$C_{12}$)-cycloalkyl.

5. The monophosphite compound according to claim 1, wherein Y is —($C_1$-$C_{12}$)-alkyl, —($C_6$-$C_{20}$)-aryl or —($C_3$-$C_{12}$)-cycloalkyl.

6. The monophosphite compound according to claim 1, wherein $R^1$ and $R^8$ are not the same radical.

7. The monophosphite compound according to claim 1, wherein X is a radical of formula (X1):

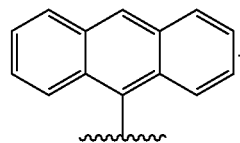

(X1)

8. The monophosphite compound according to claim 1, wherein X is a radical of formula (X2):

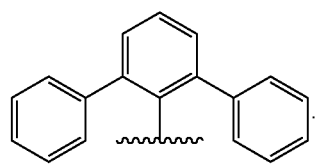

(X2)

9. The monophosphite compound according to claim 1, wherein Y is a radical of formula (Y1):

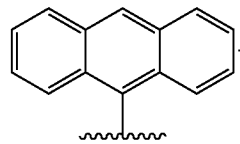

(Y1)

10. The monophosphite compound according to claim 1, wherein Y is a radical of formula (Y2):

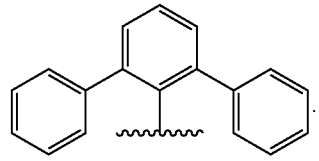

(Y2)

11. The monophosphite compound according to claim 1, wherein the compound is of structure (I).

12. The monophosphite compound according to claim 1, wherein the compound is of structure (II).

13. A metal complex, comprising:
   the monophosphite compound according to claim 1; and
   a metal selected from the group consisting of Rh, Ru, Co and Ir.

14. A method for hydroformylation comprising:
   conducting the hydroformylation reaction in the presence of a metal complex of claim 13.

15. The method for hydroformylation of claim 14, further comprising:
   a) charging an olefin to a reaction device;
   b) adding the catalyst comprising the metal complex to the reaction device;
   or adding a catalyst comprising a monophosphite compound of structure (I) or structure (II):

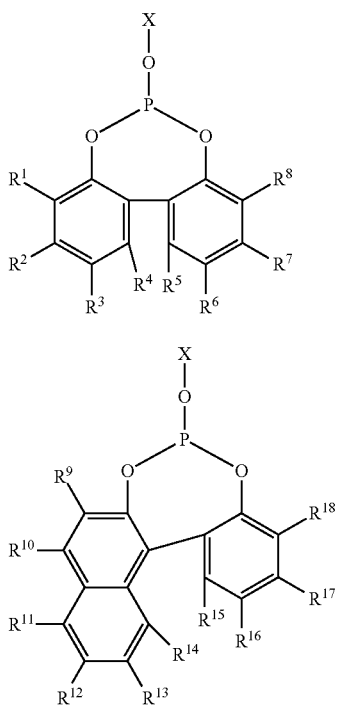

(I)

(II)

and a substance having a metal atom selected from the group consisting of Rh, Ru, Co and Ir;

c) feeding $H_2$ and CO into the reaction device to the olefin and catalyst to obtain a reaction mixture; and d) heating the reaction mixture to effect conversion of the olefin to an aldehyde;

wherein $R^1$, $R^2$, $R^3$, $R^4$, $R^5$, $R^6$, $R^7$, $R^8$ are each independently —H, —($C_1$-$C_{12}$)-alkyl, —O—($C_1$-$C_{17}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —SO$_3$H, —CN, —NH$_2$ or —N[($C_1$-$C_{12}$)-alkyl]$_2$;

$R^9$, $R^{10}$, $R^{11}$, $R^{12}$, $R^{13}$, $R^{14}$, $R^{15}$, $R^{16}$, $R^{17}$, $R^{18}$ are each independently —H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_2$)-alkyl, CONH—($C_1$-$C_{12}$)-alkyl, —CO—($C_1$-$C_{12}$)-alkyl, —CO—($C_6$-$C_{20}$)-aryl, —COOH, —OH, —SO$_3$H, —NH$_2$ or —N[($C_1$-$C_{12}$)-alkyl];

X and Y are each —($C_1$-$C_{12}$)-alkyl, —($C_6$-$C_{20}$)-aryl, —($C_3$-$C_{12}$)-cycloalkyl, or —($C_3$-$C_{12}$)-heterocycloalkyl, wherein the two R radicals in at least one of the four following radical pairs are not the same: $R^1$ and $R^8$, $R^2$ and $R^7$, $R^3$ and $R^6$, $R^4$ and $R^5$;

and the $R^3$ and $R^4$ radicals are not joined to one another via a carbon chain;

wherein when any of $R^1$ to $R^{18}$ comprises any of an alkyl and an aryl group, the alkyl group and the aryl group may optionally be substituted.

16. The method for hydroformylation of claim 15, wherein the olefin is a monoolefin having 2 to 24 carbon atoms.

17. The method for hydroformylation of claim 15, wherein the monoolefin is a terminal olefin or an internal olefin.

18. The method for hydroformylation of claim 15, wherein the catalyst comprises monophosphite compound not complexed to a metal.

19. The method for hydroformylation of claim 15, wherein the metal is Rh.

* * * * *